(12) United States Patent
Kuang et al.

(10) Patent No.: US 10,716,955 B2
(45) Date of Patent: Jul. 21, 2020

(54) METHODS AND SYSTEMS FOR IMAGE-GUIDED RADIATION THERAPY

(71) Applicant: The Board Of Regents Of The Nevada System Of Higher Education On Behalf Of The University Of Nevada, Las Vegas, Las Vegas, NV (US)

(72) Inventors: Yu Kuang, Las Vegas, NV (US); Hui Wang, Las Vegas, NV (US)

(73) Assignee: The Board Of Regents Of The Nevada System Of Higher Education On Behalf Of The University of Nevada, Las Vegas, Las Vegas, NV (US)

( * ) Notice: Subject to any disclaimer, the term of this patent is extended or adjusted under 35 U.S.C. 154(b) by 227 days.

(21) Appl. No.: 15/751,096

(22) PCT Filed: Aug. 10, 2016

(86) PCT No.: PCT/US2016/046266
§ 371 (c)(1),
(2) Date: Feb. 7, 2018

(87) PCT Pub. No.: WO2017/027547
PCT Pub. Date: Feb. 16, 2017

(65) Prior Publication Data
US 2018/0236267 A1     Aug. 23, 2018

Related U.S. Application Data

(60) Provisional application No. 62/358,394, filed on Jul. 5, 2016, provisional application No. 62/203,240, filed on Aug. 10, 2015.

(51) Int. Cl.
*A61N 5/10*     (2006.01)
*G01T 1/24*     (2006.01)
(Continued)

(52) U.S. Cl.
CPC ............ *A61N 5/1049* (2013.01); *A61B 6/032* (2013.01); *A61B 6/037* (2013.01); *A61B 6/4417* (2013.01);
(Continued)

(58) Field of Classification Search
CPC ....... A61B 6/032; A61B 6/037; A61B 6/4258; A61B 6/4417; A61B 6/481; A61B 6/482;
(Continued)

(56) References Cited

U.S. PATENT DOCUMENTS 6,838,672 B2    1/2005    Wagenaar et al.
6,950,492 B2    9/2005    Besson
(Continued)

OTHER PUBLICATIONS

International Search Report and Written Opinion dated Oct. 21, 2016 by the International Searching Authority for Patent Application No. PCT/US2016/046266, which was filed on Aug. 10, 2016 and published as WO 2017/027547 on Feb. 16, 2017 (Inventor—Kuang et al.; Applicant—The Board of Regents of the Nevada System of Higher Education on Behalf of the University of Nevada;) (13 pages).
(Continued)

*Primary Examiner* — Mark R Gaworecki
(74) *Attorney, Agent, or Firm* — Ballard Spahr LLP

(57) ABSTRACT

A radiation therapy system is equipped with a combined imaging system, such as an imaging system combining computed tomography (CT), spectral CT, and single photon emission tomography imaging (SPECT), for guidance of radiation beams providing radiotherapy. The system can include at least one x-ray source that emits an x-ray beam at a low energy level for imaging and/or an x-ray beam at a high energy level for radiation therapy. The system can also include at least one imager, such as a cadmium zinc telluride (CZT) or cadmium telluride (CdTe) flat-panel imager that receives x-ray beams traversing a subject from the x-ray (Continued)

source and gamma rays emitted by radioisotope tracers injected into the subject. Based on the guidance of the triple images (CT, spectral CT, and SPECT), a computer system can control the radiation therapeutic beam delivery to target areas, such as lesions and/or tumors.

24 Claims, 23 Drawing Sheets

(51) Int. Cl.
G01T 1/164 (2006.01)
A61B 6/03 (2006.01)
A61B 6/00 (2006.01)

(52) U.S. Cl.
CPC ............ *A61B 6/508* (2013.01); *A61B 6/5235* (2013.01); *A61N 5/107* (2013.01); *A61N 5/1039* (2013.01); *A61N 5/1067* (2013.01); *G01T 1/1642* (2013.01); *G01T 1/249* (2013.01); *A61B 6/4258* (2013.01); *A61B 6/481* (2013.01); *A61B 6/482* (2013.01); *A61N 2005/1052* (2013.01); *A61N 2005/1061* (2013.01); *A61N 2005/1062* (2013.01)

(58) Field of Classification Search
CPC .... A61B 6/508; A61B 6/5235; A61N 5/1039; A61N 5/1049; A61N 5/1067; A61N 5/107; A61N 2005/1052; A61N 2005/1061; A61N 2005/1062; G01T 1/1642; G01T 1/249

See application file for complete search history.

(56) References Cited

U.S. PATENT DOCUMENTS

| | | | |
|---|---|---|---|
| 8,873,710 B2 | 10/2014 | Ling et al. | |
| 2005/0082491 A1* | 4/2005 | Seppi | A61B 6/032 |
| | | | 250/370.11 |
| 2006/0015330 A1 | 1/2006 | Kim | |
| 2008/0009731 A1* | 1/2008 | Maschke | A61B 5/6833 |
| | | | 600/439 |

OTHER PUBLICATIONS

International Preliminary Report on Patentability dated Feb. 13, 2018 by the International Searching Authority for Patent Application No. PCT/US2016/046266, which was filed on Aug. 10, 2016 and published as WO 2017/027547 on Feb. 16, 2017 (Inventor—Kuang et al.; Applicant—The Board of Regents of the Nevada System of Higher Education on Behalf of the University of Nevada;) (12 pages).

* cited by examiner

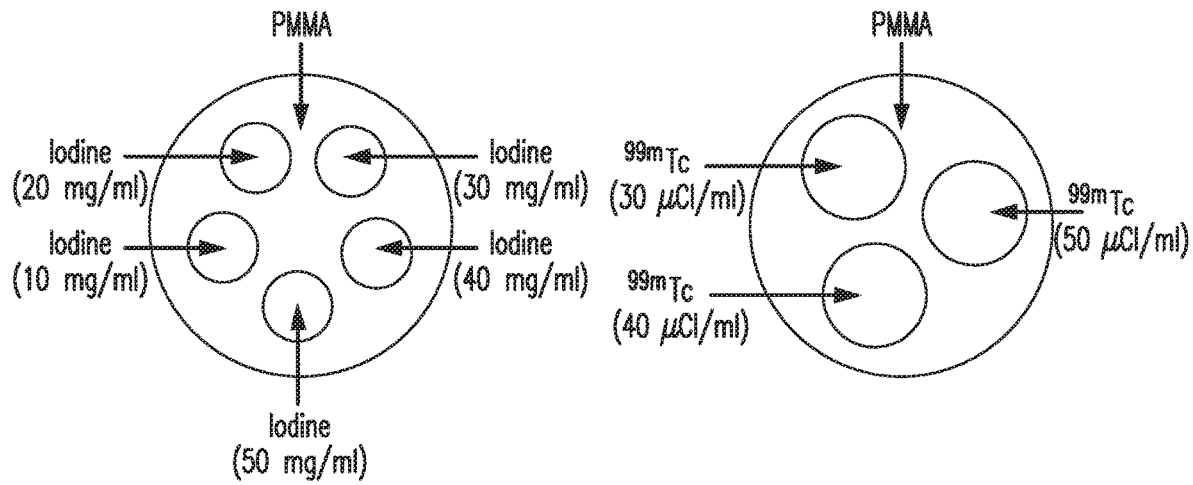
FIG. 6A
FIG. 6B
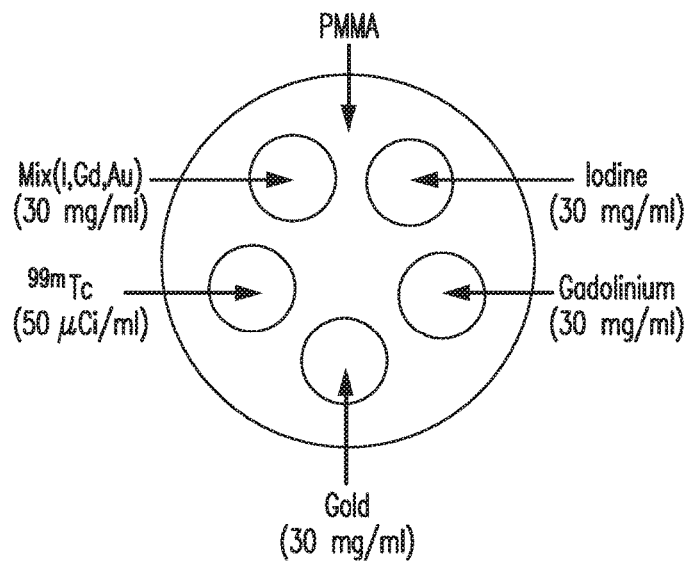
FIG. 6C

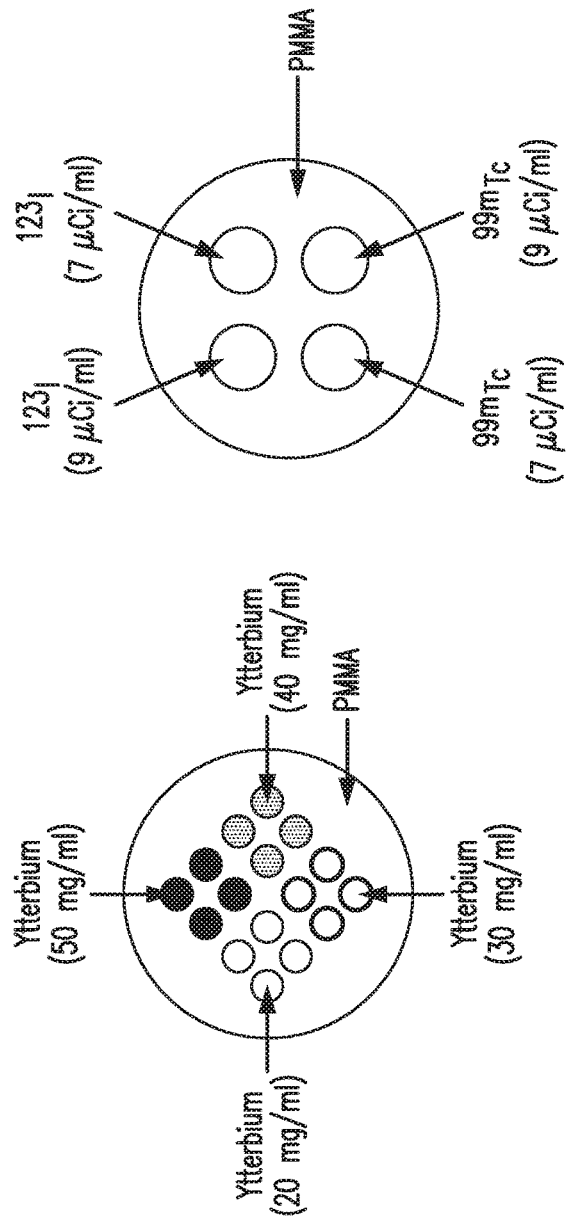
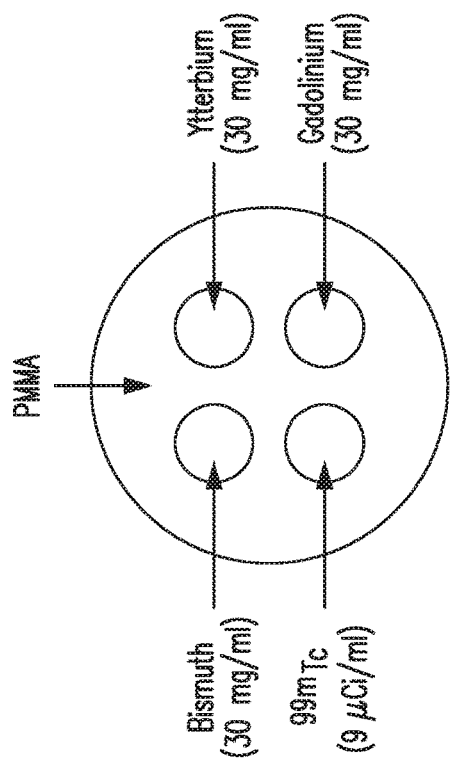
FIG. 16A
FIG. 16B
FIG. 16C

METHODS AND SYSTEMS FOR IMAGE-GUIDED RADIATION THERAPY

CROSS-REFERENCE TO RELATED APPLICATIONS

This application is a national phase application of International Application No. PCT/US2016/046266 filed on Aug. 10, 2016 which claims priority to and the benefit of the filing date of: U.S. Provisional Patent Application No. 62/203,240, filed Aug. 10, 2015, and (2) U.S. Provisional Patent Application No. 62/358,394, filed Jul. 5, 2016. The content of these earlier filed patent applications are hereby incorporated by reference in their entirety.

TECHNICAL FIELD

This document generally describes technology related to radiation based diagnostics and radiation therapy.

BACKGROUND

Radiation therapy has been used as a clinical treatment for many types of cancers, which have varying mortality rates. Image-guided radiation therapy (IGRT) has become an indispensable method for treating many cancers. Several methods and techniques for radiation therapeutic beam delivery have been developed and performed in clinical practice and preclinical research, including methods and techniques for human and animal subjects.

Currently, real-time imaging guidance during radiation therapy is predominately achieved by using on-board kilovoltage (kV) and megavoltage (MV) X-ray imaging systems, including MV, kV planar imaging and conventional KV cone-beam computed tomography (CBCT) imaging, in a medical linear accelerator (Linac). However, there are some limitations in these conventional IGRT architectures.

Firstly, although kV- and MV-images have helped define the gross target volume (GTV) of tumors, they cannot "see" the whole clinical target volume (CTV), which includes the GTV as well as all microscopic tumor extensions and subpopulations in the neighboring tissue, due to their limited detection sensitivity of tumor cells. For treatment planning, assumptions and guesses must be made about the CTV based on clinical or pathological experience, which in turn leads to a high degree of uncertainty in the CTV.

Secondly, most tumors are subjected to shape and spatial position changes during the course of the radiotherapy. To date, radiation oncologists have dealt with this problem by extending the CTV with appropriate safety margins, which are again guesses based on clinical experience. More often than not, these safety margins include large portions of healthy tissue within the high dose volume, which often means that more healthy tissue than tumor tissue is irradiated.

Thirdly and most importantly, up until recently, radiation oncologists largely assumed that the tumor consists of homogenous cancerous tissue, and therefore a homogeneous dose distribution was delivered to the target. However, more recent research has shown that a tumor may consist of subvolumes with very different radiobiological properties, such as hypoxic areas known to be highly radio-resistant, or regions with uncontrolled cellular proliferation, which is one of the hallmarks of malignant tumors. Other important molecular processes include apoptosis, which is a major form of cell death induced by radiation, and angiogenesis, the formation of new blood vessels from pre-existing vasculature, which is an essential step in tumor progression and metastasis. The heterogeneity of these molecular profiles within a tumor region is invisible by current onboard imaging systems, thus posing the challenge of delivering inhomogeneous doses to subvolumes of tumor with different radiosensitivities.

Thus, the current model for real-time IGRT using on-board KV- and MV-imaging and conventional CBCT has significant limitations, and there is a need in the art for IGRT systems and methods that provide improvements in targeting accuracy, dose distribution, and/or clinical outcomes in cancer treatment.

For current preclinical small animal radiation therapy research, imaging guidance during radiation therapy is mainly performed by using conventional CBCT imaging systems. As mentioned above with respect to human radiation therapy, the lack of chemical and molecular imaging information of small animals for radiation guidance in the current systems place similar limitations on small animal radiation studies, which are very important to clinical practice. Therefore, improved IGRT systems and methods are needed for accurate and efficient radiation therapy treatment studies of small animals.

SUMMARY

This document generally describes radiotherapy systems that can be configured to use and combine multiple different types of imaging, such as conventional-computed tomography (CT), spectral-CT, and single photon emission computed tomography (SPECT) imaging, to guide the delivery of radiotherapy beams to subjects, including human subjects and small animal subjects. Such systems can provide more detailed imaging of subjects, which can help improve the accuracy and detail with which radiotherapy beams can be delivered to the subjects.

In one aspect, a radiotherapy system includes at least one radiation source that can be configured to emit a radiation beam for (i) imaging a subject and (ii) providing radiotherapy treatment to the subject; at least one imager that can be positioned opposite a corresponding radiation source to detect the radiation beam after the radiation beam has traversed the subject, wherein the imager can be configured to detect a plurality of different types of images of the subject; a computer system that can be programmed to: combine the plurality of different types of images of the subject into a comprehensive image of the subject; identify one or more target areas within the subject for treatment based, at least in part, on the comprehensive image of the subject; determine one or more treatment characteristics for the one or more target areas based, at least in part, on the comprehensive image of the subject and the one or more target areas; and control delivery of the radiotherapy treatment by the radiation source to the one or more target areas within the subject according to the one or more treatment characteristics.

In another aspect, the radiotherapy system can include two distinct radiation sources. A first radiation source can be configured to produce a first radiation beam for imaging the subject and a second radiation source can be configured to provide a radiation therapy treatment to the subject. In this aspect, imaging and treatment of a target area of a subject can be sequential as in the single radiation source aspect. In addition, or in the alternative, the two radiation sources can provide simultaneous imaging and treatment.

The radiotherapy systems disclosed herein can optionally include one or more of the following features. For example, the plurality of different types of images can be a conventional-CT image type, a spectral-CT image type, and a SPECT image type. The radiotherapy system can further include a collimator that can be positioned between the imager and the subject, and that can be configured to direct one or more types of radiation from the subject to the imager. The one or more types of radiation can be gamma rays, and the imager can be configured to detect the gamma rays. The subject can be injected with one or more radioisotopes that emit the one or more types of radiation. The collimator can be a high resolution collimator with one or more surfaces defining holes that can be specifically sized or shaped. The holes can be sized to correspond to the size of pixels in the imager. The high resolution collimator can be a parallel square-hole collimator.

The imager can be a photon counting imager that can be configured to receive photons from the radiation beam that have traversed the subject. The photon counting imager can be a cadmium zinc telluride (CZT) imager. The radiation source can be an x-ray radiation source and the radiation beam can comprise an x-ray beam. The x-ray radiation source can be an x-ray tube. The radiation source can be configured to emit the radiation beam (i) at one or more low energy levels for imaging the subject and (ii) at one or more high energy levels to provide the radiotherapy to the subject. The imager can detect the plurality of different types of images of the subject in advance of the radiotherapy treatment being delivered to the subject.

The imager can detect the plurality of different types of images in the subject while the radiotherapy treatment can be delivered to the subject, and the computer system can be programmed to repeatedly perform the combining, the identifying, the determining, and the controlling while the radiotherapy treatment is delivered. The radiotherapy system can further include a gantry that can be rotatable about a central axis and to which the at least one radiation source and the at least one imager can be mounted. The computer system can be further programmed to control rotation of the gantry according to the one or more treatment characteristics. The radiotherapy system can further include a moveable support structure for the subject. The computer system can be further programmed to control movement of the moveable support structure.

Certain implementations may provide one or more advantages. For example, using combined imaging systems to guide the delivery of radiotherapy beams can improve the accuracy and effectiveness of the radiotherapy treatment. In another example, by integrating an on-board imaging system that can be capable of multiple different types of imaging, such as triple imaging including conventional-CT, spectral-CT, and SPECT, into a radiotherapy platform using the same radiation source (e.g., x-ray source) and the same imager (e.g., CZT imager), the same geometry coordinates can be used for both imaging and treatment, which can provide for more accurate treatment without additional errors from image registration.

In a further example, the disclosed image-guided radiotherapy systems can provide comprehensive structure/anatomy, chemical composition, and molecular imaging of subjects for precise delineation of 3D structures and/or contours of lesion and/or other targets within subjects.

In another example, image-guided radiotherapy systems can produce KV planar images with spectral information based on a photon counting imager during the treatment, which can improve both the detail of the imaging and the accuracy of the radiotherapy. For instance, using different energy windows, tissue types and/or constituents that can be of interest (e.g., lesions, tumors) can be highlighted, which can improve the accuracy with which treatment beam can be directed to specific targets (e.g., lesions, tumors) through fine adjusting various factors during treatment, such as the beam position, the beam characteristics, and/or the position of a subject during the treatment.

In a further example, evaluation of the therapeutic effects of radiation and tissue response to the therapy can be determined through imaging of the multiple features of target areas (e.g., lesions, tumors), which can be used to more accurately and timely adjust dosages (and other treatment characteristics) during the course of treatment.

In another example, contrast agents used in spectral CT imaging can also act as radio-sensitizing agents in radiation therapy. For example, gold element contained contrast agents (such as gold nanoparticles) that have high relative photoelectric cross sections compared to water, which can results in a significant enhancement of local radiation dosages. Simultaneously, these agents can be used to enhance spectral CT imaging contrast due to the high atomic number of gold element. These features can enhance and improve both imaging and therapy from radiotherapy systems, particularly over anatomical image-guided radiotherapy techniques.

In a further example, more accurate imaging guidance for radiation therapy beams can be provided by using an imager capable of directly and electronically converting x-ray and gamma rays through pixilation based on semiconductor detectors used in radiotherapy systems, as opposed to less accurate imaging guidance that can result from electronic imagers that indirectly convert based on scintillators.

In various exemplary aspects, a gantry-based conventional CT, spectral CT and SPECT triple onboard IGRT system can be provided by integrating a single photon counting detector panel into a Linac assembly, with the photon counting detector panel being mounted to the Linac within the treatment room. In these aspects, the photon counting detector panel can replace the conventional kV-beam X-ray flat panel detector and use the exact same coordinate system/position of kV-beam X-ray flat panel detector. In further aspects, the photon counting detector panel can be a pixelated CZT imager, and a gamma ray collimator can be attached in front of the imager for SPECT imaging. In exemplary uses, the disclosed triple onboard IGRT system can be used to provide image-guided radiation treatment to human subjects.

In use, the disclosed triple onboard IGRT system can advantageously integrate spectral CT imaging, which provides contrast-enhanced anatomical imaging with lower dosages and molecular imaging via targeted nanoparticles, such as gold nanoparticles, and SPECT imaging that provides molecular imaging via targeted radio-probes into the Linac for precisely guiding the radiation treatment processes. It is contemplated that this integration can provide oncologists with the ability to detect cancer by identifying cellular characteristics, tissue functions and biochemistry/metabolism that change long before a cancer grows to a size detectable by conventional anatomical imaging modalities (including kV planar imaging and CBCT). Based on three-dimensional (3D) molecular imaging of the tumors, the oncologists can pinpoint the precise location and volume/contour of the tumors and personalize treatment radiation fields such that the tumors can be therapeutically treated while the healthy tissues are spared to the maximal degree.

In use, it is further contemplated that the disclosed triple onboard IGRT system can provide structure/anatomy (kV imaging and CBCT, the CZT imager working at integration mode) and dual-molecular (spectral-CT/SPECT, the CZT imager working at pulse-counting mode) information using the same on-board CZT imager, with tissue function information defined within the anatomic context, which is important to understand diseases more accurately. In addition, because the co-registration of biological and anatomical information in the treatment room is based on the same coordinates, it is contemplated that additional errors from image registration can be avoided.

In use, it is still further contemplated that the disclosed triple onboard IGRT system can permit imaging of multiple probes concurrently prior to and during the course of radiotherapy to provide sufficient sensitivity and specificity to delineate tumors efficiently for radiotherapy. The targeted probes include radiolabeled isotopes for SPECT imaging, such as targeted $^{99m}$Tc and $^{123}$I, and non-radiolabeled high atomic number metal elements for spectral CT imaging, such as the following element-tagged nanoparticles: iodine (K-shell energy=33.2 keV), gadolinium (K-shell energy=50.2 keV), ytterbium (K-shell energy=61.3 keV), gold (K-shell energy=80.7 keV), and bismuth (K-shell energy=90.5 keV). In use, it is still further contemplated that the disclosed triple onboard IGRT system can advantageously produce projection images with spectral information based on a photon-counting CZT imager with a high-energy resolution during the radiation treatment. Using the different energy windows, it is contemplated that the targeted tissue types or constituents can be highlighted, which can help accurately direct the treatment beam to the specific target The details of one or more embodiments are set forth in the accompanying drawings and the description below. Other features and advantages will be apparent from the description and drawings, and from the claims.

DESCRIPTION OF DRAWINGS

FIGS. 6A-6C depict various phantoms that were used in simulations to investigate the performance of an on-board triple IGRT system as disclosed herein.

FIGS. 16A-16C show phantoms used in the simulations to investigate the performance of convention-CT/spectral-CT/SPECT imaging according to an embodiment. The phantoms include four groups of ytterbium inserts with four different concentrations in a polymethylmethacrylate (PMMA) cylinder, two isotopes of $^{99m}$Tc and $^{123}$I inserts with two different radiation activities in a PMMA cylinder, and four multiple contrast (including gadolinium, ytterbium, bismuth, and a radiation source from $^{99m}$Tc) inserts in a PMMA cylinder.

FIG. 17A is a sinogram from the detection of the ytterbium inserts. FIG. 17B is a reconstruction image from the sinogram data. FIG. 17C shows the average pixel values of the four groups inserts.

FIGS. 18A-18B show the sinogram and reconstruction image of the dual isotope inserts from the spectrum range of 130 keV to 170 keV of the detection projections. FIGS. 18C-18D show the sinogram and reconstruction image of the $^{99m}$Tc inserts from the spectrum range of 130 keV to 150 keV of the detection projections. FIGS. 18E-18F show the sinogram and reconstruction image of the $^{123}$I inserts from the spectrum range of 150 keV to 170 keV of the detection projections. FIG. 18G shows an overlay of the images of the $^{99m}$Tc and $^{123}$I inserts, wherein the $^{99m}$Tc and $^{123}$I inserts can be displayed with red and green color, respectively. FIG. 18H shows average pixel values of the inserts with different radiation activities.

FIGS. 19A-19F and 19G-19H show the spectral CT reconstruction images and the conventional CT reconstruction images and the corresponding image CNRs of the gadolinium, ytterbium, bismuth inserts in the phantom, respectively.

DETAILED DESCRIPTION

Figure 1:
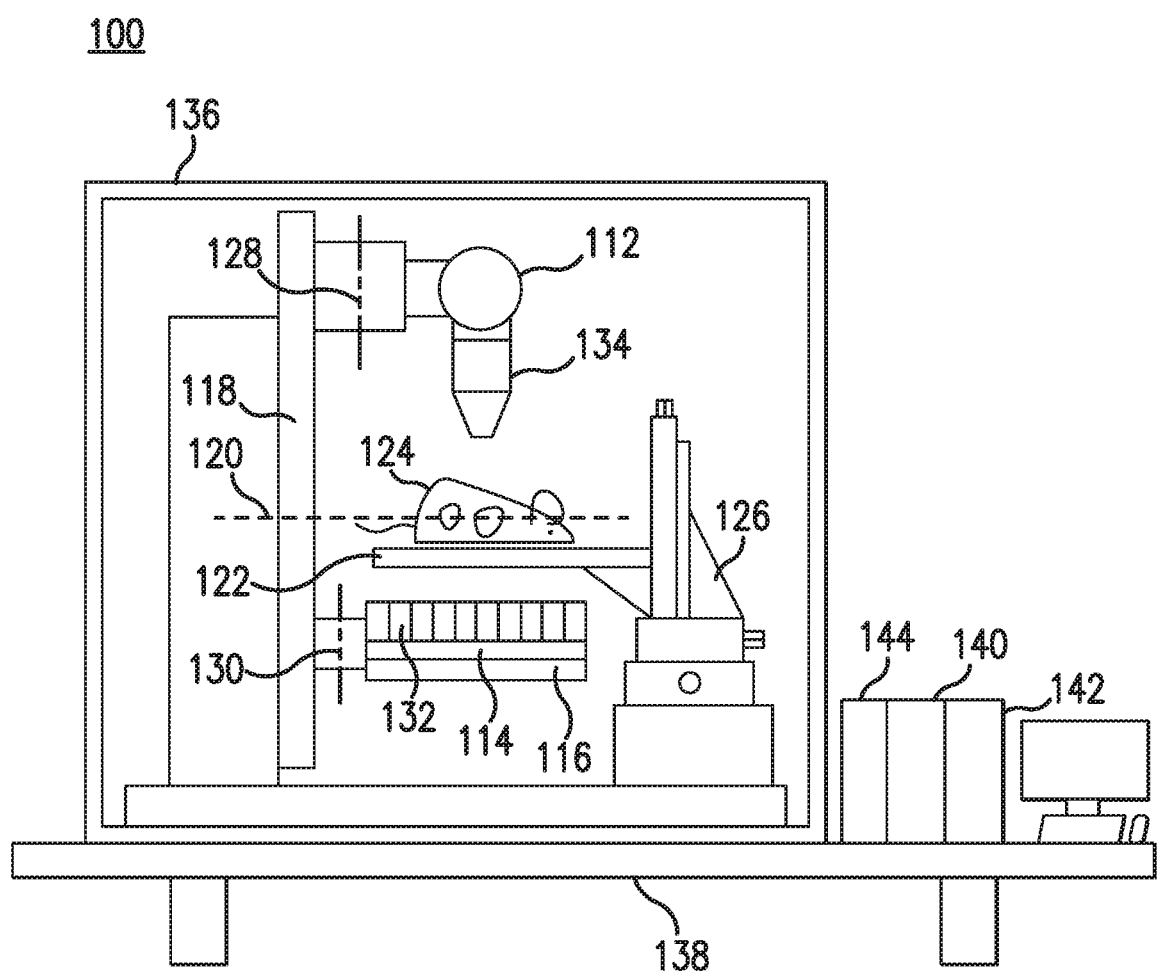
FIG. 1 depicts a side view of an example radiation therapy system that uses multiple combined imaging techniques to guide radiation therapy treatment for a subject (e.g., a small subject).

The present disclosure can be understood more readily by reference to the following detailed description, examples, drawing, and claims, and their previous and following description. However, before the present devices, systems, and/or methods can be disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

The following description of the disclosure is provided as an enabling teaching of the disclosure in its best, currently known embodiment. To this end, those skilled in the relevant art will recognize and appreciate that many changes can be made to the various aspects of the disclosure described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure can be possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to "a radiation source" can include two or more such radiation sources unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

By a "subject" is meant an individual. The term subject can include humans and can also include small or laboratory animals as well as primates. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

As used herein with respect to computed tomography (CT), the term "conventional" refers to a standard CT method and implementation using X-rays with a whole spectral energy range, which makes use of a radiation source to produce an image. For example, during a conventional CT scan, computer-processed combinations of many X-ray projection images can be taken from different angles to produce cross-sectional (tomographic) images (virtual "slices") of specific volumes of a scanned object (e.g., subject), whereas spectral CT is a new modality of computed tomography that uses X-rays with multiple energy bins or windows to produce spectral CT images of a scanned object (e.g., subject) usually based on injected particles with high atomic number elements. The use of the term "conventional CT" does not infer that any other aspect of the disclosure is known or conventional.

Conventional CT techniques have been used to generate high quality imaging of anatomical structures of human and animal subjects. Conventional CT has used detectors operated in an integration mode and has been limited by the energy resolution being insufficient to reveal the spectral information of energy-dependent radiation absorption of the scanned subject. Conventional CT has also provided low soft tissue contrast. Spectral CT is a newly emerging CT technique, which has been developed from the conventional CT technique. Spectral CT, particularly based on the photon counting detectors, provides high energy resolution so that it can reveal the spectral information indicative of element composition of the scanned subject. Spectral CT can provide chemical analysis of tissue relating to functional- and molecular-level processes. SPECT techniques can be used as a nuclear imaging method for studying molecular biological processes in human and animal subjects.

Radiation Therapy Systems and Methods

This document generally describes combining multiple imaging techniques, such as conventional CT, spectral CT, and SPECT, within an on-board imaging system for radiation therapy systems (e.g., a medical linear accelerator) to provide structural, chemical, and molecular imaging of subjects, and to guide radiation therapy provided to subjects. In use, it is contemplated that the combination of conventional CT, spectral CT, and SPECT in a triple on-board imager system can provide structural, chemical and molecular imaging of human and animal subjects. Also described herein are triple image-guided radiotherapy systems and methods that make use of the triple on-board imager.

The parameters of the system can be attuned to alter the levels of radiation applied to a given subject during diagnostic imaging and treatment. In exemplary aspects, and as further disclosed herein, the system can be used to image and provide therapy to human subjects. However, in other aspects, it is contemplated that, with the adjustment of various system parameters, the disclosed systems can be used to image and provide therapy to animal subjects (e.g., small animal subjects).

Image-guided radiotherapy platforms described in this document can use and combine multiple radiation imaging techniques to increase the detail with which structures can be detected within subjects. Additionally, the imaging can be performed using the same equipment and from the same vantage point as the radiotherapy delivery system, which can allow for the images that can be obtained to be within the same frame of reference for the radiotherapy delivery system. This can allow for more precision and accuracy in the delivery of radiotherapy to subjects. Instead of having to translate coordinates, scales, and orientations of images of a subject from a vantage point that can be different from that of the radiotherapy delivery system, which can be a possible source for additional errors, the same vantage point, scale, and orientation of the subject can be used for both imaging and therapy, which can increase the precision and accuracy of the radiotherapy.

Any of a variety of different imaging techniques can be combined for use in an image-guided radiotherapy platform. For example, a platform can combine conventional CT, spectral-CT, and SPECT imaging to provide guidance for radiotherapy as part of the platform. A variety of different configurations can be possible. Subjects can be imaged using radiation sources (e.g., x-ray tubes) that emit radiation beams (e.g., x-ray beams) with low energy levels in any of a variety of forms (e.g., cone-beam forms) towards a subject, and imagers (e.g., CZT imager) can receive the radiation beams after they traverse the subject. To provide radiation therapy to subjects, after adjusting a subject to a proper position based on imaging information (e.g., combination of conventional-CT, spectral-CT, and/or SPECT images) radiation sources can emit radiation beams (e.g., x-ray beams) with high energy levels, and one or more collimators can be used to tailor the beams to appropriate sizes and/or shapes towards treatment target volumes within subjects. Depending on treatment situations, the tailored radiation sources (e.g., x-ray sources) can rotate around the treatment target and/or remain stationary. One or more computing devices can interface with motion controllers based on the information of acquired and reconstructed images of the subject to realize image-guided radiotherapy.

Any of a variety of appropriate techniques can be used to provide image-guided radiation treatment for human subjects. For example, image-guided radiation treatment of lesions and/or other targets can include performing and combining multiple different types of imaging, such as conventional-CT imaging, spectral-CT imaging, and/or SPECT imaging. The imaging can be used to identify and define one or more target volumes for radiotherapy, to determine beam geometry characteristics for the radiotherapy, to select one or more appropriate dose prescriptions, and/or to guide delivery of the treatment beam through rotating the high level energy x-ray beam around the target. Any of a variety of appropriate techniques can be used as part of the image-based treatment planning and delivery, such as a Monte Carlo dose calculation technique. Any of a variety of appropriate imagers can be used to obtain multiple types of images, such as a CZT imager. Additionally, imaging (e.g., conventional CT, spectral CT, SPECT) of a target can be performed in advance of and/or during treatment, and can be used to adjust the motion of the radiation source and the position of the subject accordingly.

As further disclosed herein, the radiotherapy modalities can be implemented on a radiotherapy system. In an example embodiment, the radiotherapy system can include at least one radiation source, at least one imaging subsystem (e.g., at least one imager), and a computing system to monitor and control the radiation sources and the imaging subsystems. Optionally, in an aspect of the embodiment, the system can include multiple radiation sources and multiple imaging subsystems (e.g., multiple imagers). However, in an alternative aspect of the embodiment, the system can comprise a single radiation source and a single imaging subsystem (e.g., a single imager).

In an exemplary aspect, the disclosed system can comprise a gantry-based implementation of a conventional CT, spectral CT and SPECT triple onboard IGRT system by integrating a single photon counting detector panel into a current medical linear accelerator (Linac). In these aspects, the photon counting detector panel can be mounted to a Linac within the treatment room. It is contemplated that the photon counting detector panel can replace the current kV-beam X-ray flat panel detector and use the exact same coordinate system/position of kV-beam X-ray flat panel detector. In further aspects, the photon counting detector panel can be a pixelated CZT imager or a pixelated cadmium telluride (CdTe) imager, and a gamma ray collimator can be attached in front of the imager for SPECT imaging.

It is contemplated that the disclosed image-guided techniques can be useful for treating small target structures. For example, it is contemplated that the disclosed image-guided techniques can be particularly beneficial for precisely defining and more accurately positioning target radiation volumes, which can improve radiotherapy applications to target structures (e.g., lesions, tumors) and/or reduce dose deposition in the surrounding radiosensitive normal structures. Furthermore, there can be many uncertainties during the course of treatment (e.g., location variance of lesions/tumors, system errors of setup, biological processes) that can cause radiotherapy treatments to miss their intended target volume and/or to mistakenly irradiate normal critical structures. Improvements in the accuracy and comprehensiveness of imaging techniques can be used to better guide the delivery of radiation treatment beam to the target areas (e.g., lesions, tumors) within subjects, which can improve the precision of the radiotherapy, reduce the possibility of irradiating normal structures, and improve the overall results of radiotherapy.

In applying the treatment and imaging modalities to a subject varying ranges of energy levels can be used to provide the most accurate imaging results and effective radiotherapies. The physical system can be calibrated and/or configured to the appropriate energy levels for a given subject.

In exemplary aspects, the disclosed systems can integrate spectral CT imaging, which provides contrast-enhanced anatomical imaging with lower dosages and molecular imaging via targeted nanoparticles, such as gold nanoparticles, and SPECT imaging that provides molecular imaging via targeted radio-probes into the linear accelerator for precisely guiding the radiation treatment processes. This integration can provide the ability to detect cancer by identifying cellular characteristics, tissue functions and biochemistry/metabolism that change long before a cancer grows to a size detectable by conventional anatomical imaging modalities (including kV imaging and CBCT). Based on three-dimensional (3D) molecular imaging of the tumors, the oncologists can pinpoint the precise location and volume/contour of the tumors and personalize treatment radiation fields such that the tumors can be therapeutically treated while the healthy tissues can be spared to the maximal degree.

In use, the disclosed systems can provide structure/anatomy (kV imaging and CBCT, the CZT imager working at integration mode) and dual-molecular (spectral-CT/SPECT, the CZT imager working at pulse-counting mode) information using the same on-board CZT imager, with tissue function information defined within the anatomic context, which can be important for understanding diseases more accurately. In addition, because the co-registration of biological and anatomical information in the treatment room can be based on the same coordinates, additional errors from image registration can be avoided.

In use, the disclosed systems can permit imaging multiple probes concurrently prior to and during the course of radiotherapy to provide sufficient sensitivity and specificity to delineate tumors efficiently for radiotherapy. The targeted probes include radiolabeled isotopes for SPECT imaging, such as targeted $^{99m}$Tc and $^{123}$I, and non-radiolabeled high atomic number metal elements for spectral CT imaging, such as the following element-tagged nanoparticles: iodine (K-shell energy=33.2 keV), gadolinium (K-shell energy=50.2 keV), ytterbium (K-shell energy=61.3 keV), gold (K-shell energy=80.7 keV), and bismuth (K-shell energy=90.5 keV).

In use, the disclosed systems can advantageously produce projection images with spectral information based on a photon-counting CZT imager with a high-energy resolution during the radiation treatment. Using the different energy windows, the targeted tissue types or constituents can be highlighted, which helps accurately direct the treatment beam to the specific target. In use, the disclosed systems can also provide important evaluation of radiation therapeutic effects and tissue response to the therapy through imaging the multiple features of the tumors, which helps for timely dose adjustment during the treatment course.

In exemplary aspects, it is contemplated that some contrast agents used in spectral CT imaging can also act as radiosensitizing agents in the radiation therapy. For example, the gold element-containing contrast agents (such as gold nanoparticles) have high relative photoelectric cross-sections compared to water, resulting in a dramatic increase of the local dose. Simultaneously, these agents can be used in spectral CT imaging due to the high atomic number of gold. This characteristic gives the disclosed systems a unique advantage over the current anatomical image-guided radiotherapy techniques.

Systems Having Multiple Radiation Sources

In exemplary aspects, the at least one radiation source of the system can comprise a plurality of radiation sources, and the at least one imager can comprise a plurality of imagers. In these aspects, it is contemplated that each imager can be oriented toward a corresponding radiation source that is positioned on an opposing side of the subject from the imager. In exemplary aspects, and as further disclosed herein, systems comprising a plurality of radiation sources can be used to image and provide therapy to human subjects (patients).

Depicted in FIGS. 10-12D is an exemplary system 200 having at least first and second radiation sources. In exemplary aspects the system 200 can be configured to apply radiation therapy to human subjects (patients). It is contemplated that the first radiation source can be configured for diagnostics and imaging, while the second radiation source can be configured for treatment of a target site. Optionally, it is contemplated that the first and second radiation sources can be provided as distinct physical structures. In use, distinct radiation sources within system 200 provide the additional capability of monitoring a target site with one subsystem and treating the target site with another subsystem, simultaneously. In further aspects, it is contemplated that one of the first and second radiation sources can be configured to selectively deliver radiation that is sufficient to produce at least two different types of images (e.g., convention-CT images and spectral CT images). In these aspects, it is further contemplated that a corresponding one of the first and second imagers can be configured to produce the at least two different types of images.

In exemplary aspects, during imaging and treatment of human subjects (patients), it is contemplated that the first and/or second radiation sources (e.g., first and/or second X-ray sources) can be configured to provide radiation in a first range of desired energy levels for diagnostic applications and to provide radiation in a second range of desired energy levels for treatment applications. For example, in one aspect, the range of desired energy levels for diagnostic applications can range from about 70 kVp to 150 kVp. In another exemplary aspect, the range of desired energy levels for treatment applications can range from about 6 MV to 10 MV.

Figure 10:
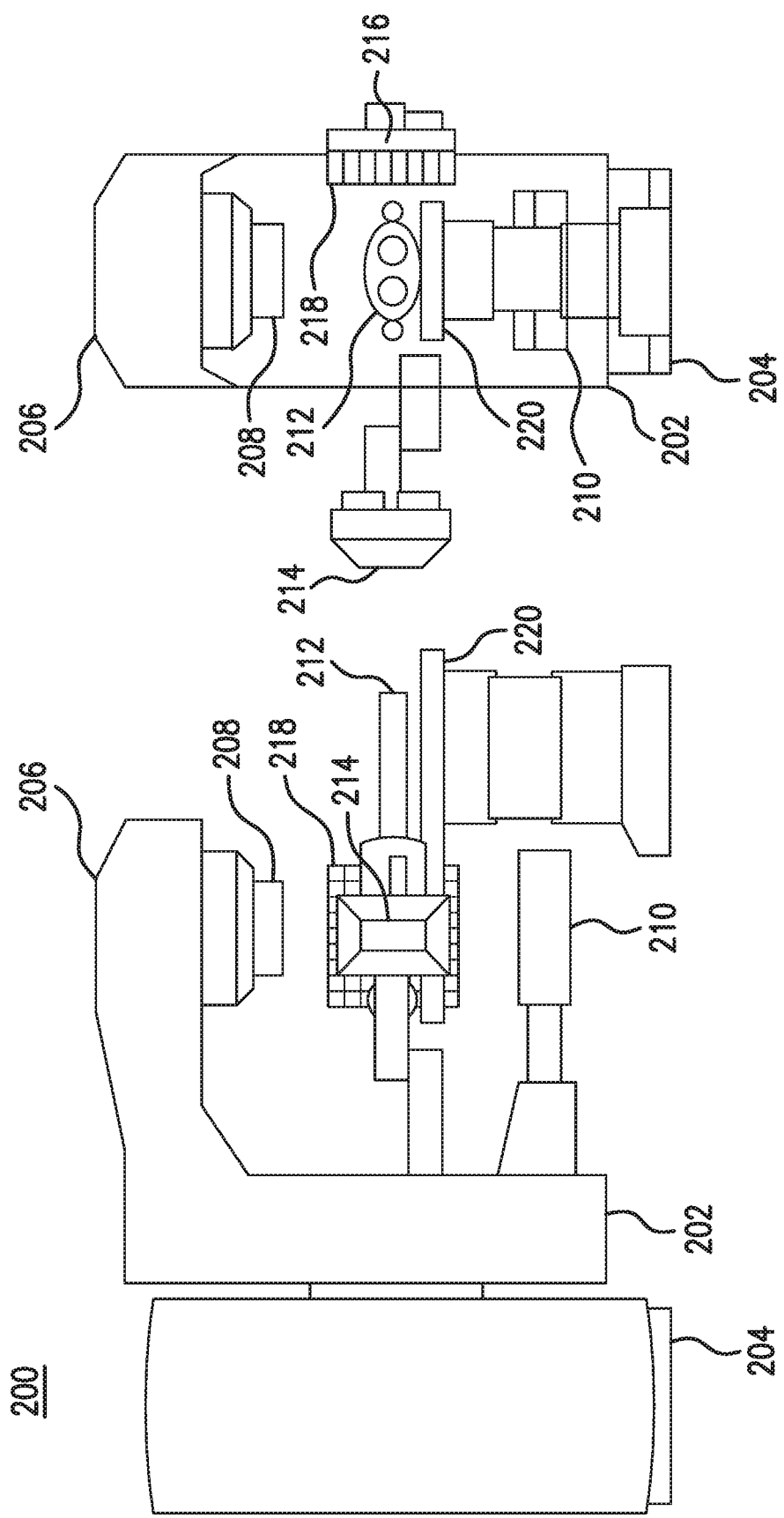
FIG. 10 illustrates an onboard conventional-CT/spectral-CT/SPECT image-guided radiotherapy system configured for multiple radiation sources used for triple image-guided treatment in subjects (e.g., human subjects).

A medical linear accelerator (Linac) 200 integrated with a conventional CT, spectral CT and SPECT triple onboard imager is shown in FIG. 10. The system 200 includes a rotatable gantry 202, supported and stabilized by a stand 204. The radiation treatment beam delivery and conventional-CT/spectral-CT/SPECT triple imaging guidance units can be attached to the gantry 202, so that they can rotate with it. Alternatively, it is contemplated that the imaging guidance units can be selectively rotatable relative to the gantry 202. The radiation treatment unit includes a MV X-ray source in the treatment head 206 of the Linac, which can be shaped and intensity-modulated by a multi-leaf collimator (MLC) 208, and an MV X-ray imager 210 that detects the transmitted photons out of MLC 208 towards a patient 212. The MV X-ray imager 210 can be selectively retractable if it is not needed in some situations and/or applications. The conventional-CT/spectral-CT/SPECT triple imaging guidance unit includes a KV X-ray tube 214, a pixelated photon counting CZT imager 216, and a gamma ray collimator 218. The distance between X-ray tube 214 and the CZT imager 216 can be changed through moving the X-ray tube 214 and/or the CZT imager 216 relative to the rotational (central) axis of the gantry 202. In exemplary aspects, the X-ray tube 214 and/or the CZT imager 216 can be selectively radially retractable if they cannot be used in some conditions and/or applications. The position of the patient 212 can be controlled by multi-dimensional motion of a treatment couch 220, wherein the subject (e.g., patient) can be selectively positioned within the central portion of the gantry 202. As used herein, the term "treatment couch" refers to any structure that is configured to support a subject (e.g., patient) during a radiotherapy treatment as disclosed herein.

Figure 11:
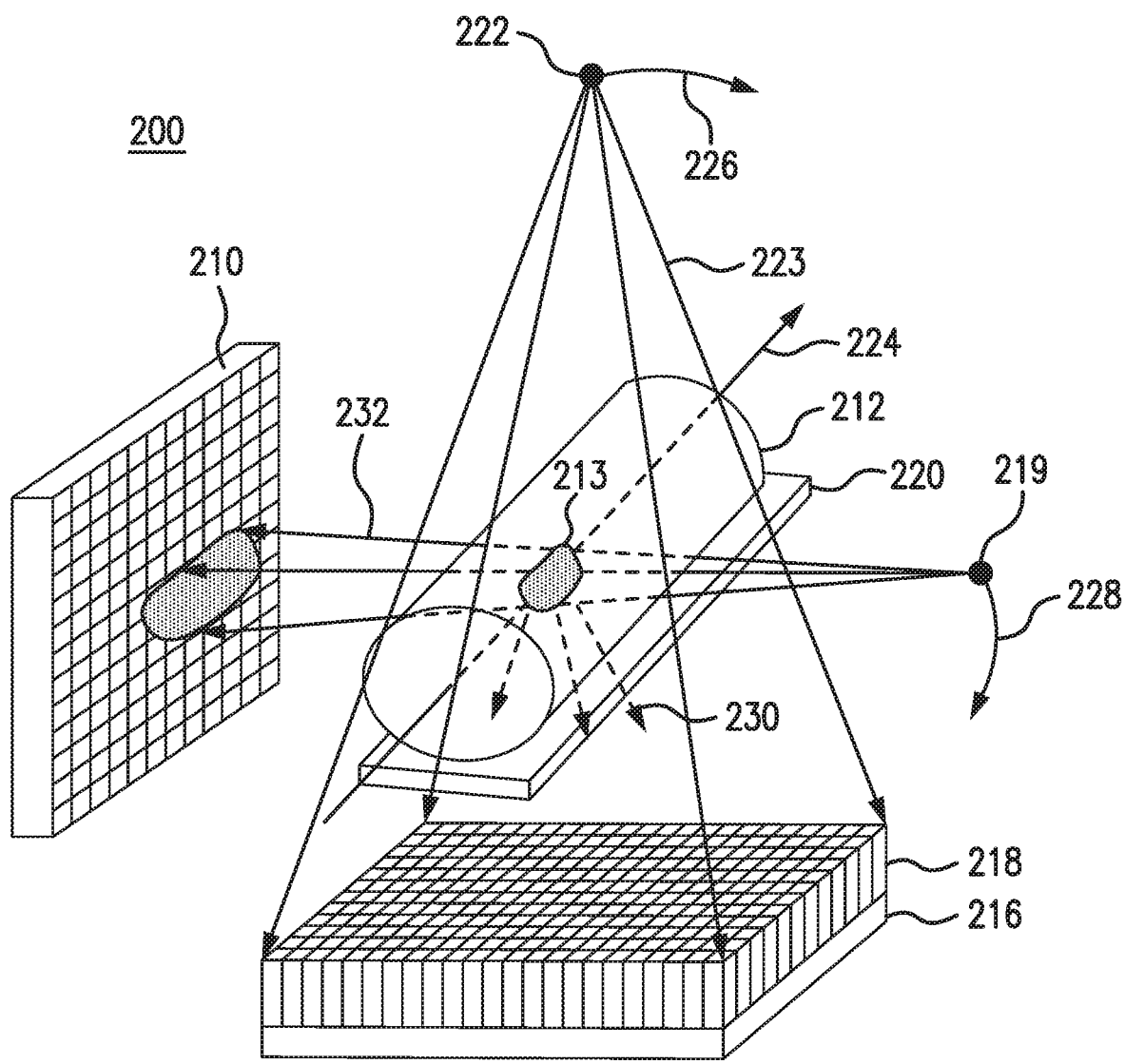
FIG. 11 schematically illustrates a perspective view of a linear accelerator (Linac) integrated with a photon counting CZT onboard imager for conventional-CT/spectral-CT/SPECT imaging guidance.

The configuration of a system 200 for providing conventional-CT/spectral-CT/SPECT triple imaging guidance along with radiation treatment beam delivery is schematically illustrated in FIG. 11, according to an exemplary embodiment of the disclosure. In conventional CT and spectral CT imaging, an X-ray source 222 emits kV cone-beam X-ray photons 223 that pass through a patient 212 on a treatment couch 220 towards a pixelated photon counting CZT imager 216. The pixelated CZT imager 216 that works in pulse-counting mode registers the energy and position of each photon that hits on it. The geometry of the kV beam X-ray imaging can be the same as that used for Cone-Beam CT (CBCT). The kV CT imaging mode can work as planar imaging, a pair of radiographs (kV/kV or MV/kV pair) or a CBCT scan. In addition, Isotope-labeled radiopharmaceuticals that aggregate to a local lesion or tumor 213 within the patient 212 can emit gamma rays 230 in all directions, and only the gamma photons perpendicular to the surface of the CZT detection elements can be detected due to the parallel-hole collimator 218 that can be positioned in front of the detection elements.

The MV X-ray beam 219 from the Linac can be tailored and intensity modulated by the MLC 208 to a narrow beam 232, which highly conforms to the range and shape of the lesion or tumor 213 within the patient 212. An MV X-ray imager 210 detects the photons that pass through the lesion or tumor 213 from the narrow beam 232, and the geometry of the MV imaging can be also the same as the CBCT. The MV imaging acquisition modes include detector readout during MV beam on, detector readout while MV beam can be paused, and integration or Intensity Modulated Radiotherapy (IMRT) or Volumetric Arc Therapy (VMAT) or RapidArc® Radiotherapy for portal dosimetry. The kV X-ray imaging geometry and the MV X-ray radiation treatment geometry can be arranged perpendicularly to each other, and can be designed to rotate around the same central axis 224 along the circle path 226 and 228, respectively.

An exemplary embodiment of the system 200 is shown in FIG. 12A-12D, including the conventional-CT/spectral-CT/SPECT diagnostic imaging and image-guided radiation treatment beam delivery. Typically, there can be two steps necessary to acquire the diagnostic conventional-CT/spectral-CT/SPECT images to guide the radiation therapy, including acquiring conventional-CT/spectral-CT projection data and acquiring SPECT projection data for image reconstruction.

Figure 12A:
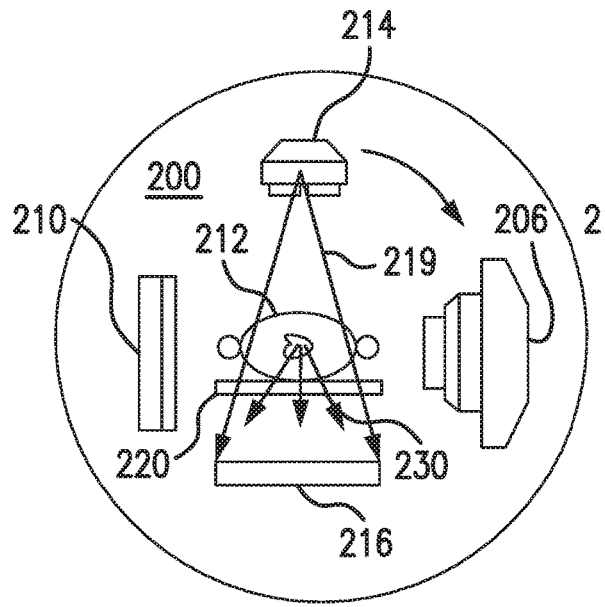
FIG. 12A illustrates an arrangement of conventional CT and spectral CT imaging to guide radiation treatment in a Linac system.

When acquiring conventional CT and spectral CT images simultaneously, as shown in FIG. 12A, the X-ray tube 222 can be turned on at a kV energy level, typically less than 140 kV. The kV X-ray beam 223 emitted from the X-ray tube 222 traverses a patient 212 towards a pixelated photon counting CZT imager 216, which records the energy and position information of each X-ray photon that interacts with each pixel. The patient 212 can be administrated with CT contrast agents containing one or more high atomic number elements or materials and isotope-labeled radiopharmaceuticals before acquiring data. It should be noted that the CZT imager 216 also detects the gamma rays 230 emitted from the radiopharmaceuticals. Due to the high energy-resolution capacity of the photon counting CZT detector, it can be easy to separate the gamma rays from the X-rays based on their energy differences.

The X-ray tube 222 and the CZT imager 216, which are attached to the gantry, rotate around the central axis of the gantry 202 of the system 200 synchronically to perform full 360-degree scanning of the patient 212 on a treatment couch 220. In exemplary aspects, the system 200 can comprise at least one rotational actuator that is operatively coupled to the gantry 202 and configured to effect selective rotation of the gantry (and the various radiation sources and imagers) relative to the central axis of the gantry. Optionally, in these aspects, the at least one rotational actuator can be communicatively coupled to a computer system as further disclosed herein such that the computer system can selectively control rotation of the gantry. Alternatively, it is contemplated that the gantry 202 can be rotated in a manual fashion to achieve a desired orientation of the radiation sources and imagers. To obtain the spectral CT image, several energy thresholds should be set to the X-ray photons acquired based on the administrated contrast elements within the patient 212. To obtain the conventional CT image, all the photons from each energy threshold can be added in each pixel. In the other words, the conventional CT reconstruction can be based on the whole spectral range X-ray photons instead of separated spectral ranges of photons in the spectral CT reconstruction. In addition, the conventional CT imaging can also be obtained by the CZT imager 216 that works in integration mode instead of pulse-counting mode.

Figure 12B:
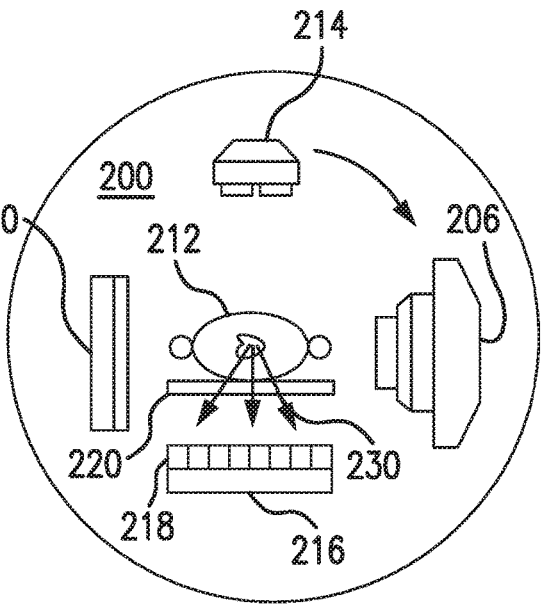
FIG. 12B illustrates an arrangement of SPECT imaging for guidance of radiation treatment in a Linac system.

When acquiring the SPECT image, as shown in FIG. 12B, the X-ray tube 222 can be turned off, and a gamma ray multi-hole collimator 218, usually made of lead, can be placed in front of the CZT imager 216 to collimate the gamma rays 230 normally directed to the surface of the imager pixels due to the isotropic emission of the gamma rays. The exemplary collimator type can be a parallel-hole collimator, where the holes of the collimator can be designed to match the size of pixel of the imager 216, but a single- or multiple-pinhole collimator can also be used. After projections can be collected similarly to conventional-CT/spectral-CT imaging, all projection data can be processed to generate tomography images that reveal the radiopharmaceutical distribution within the patient. Because of the improved energy resolution of the CZT imager over the conventional NaI imager, the radiopharmaceuticals labeled with two or more isotopes can be imaged simultaneously even if the photopeaks of these isotopes can be very close, such as $^{99m}$Tc (140 keV) and $^{123}$I (160 keV).

Furthermore, to speed up the clinical process, the acquisition mode of CZT imager can be also designed for fast image acquisition of regions of interest (ROI) of the object. The entire object can be first imaged with a quick CT scan for a short period. This provides a snapshot with a relatively low radiation dose. This quick "scout view" can then be used to define ROIs in the object. The conventional CT/spectral CT/SPECT scan could then be modified to only image the ROI, which further reduces the volume receiving radiation dose. This hybrid imaging scheme provides high quality images of the ROIs with a faster imaging time and a limited radiation dose.

Figure 12C:
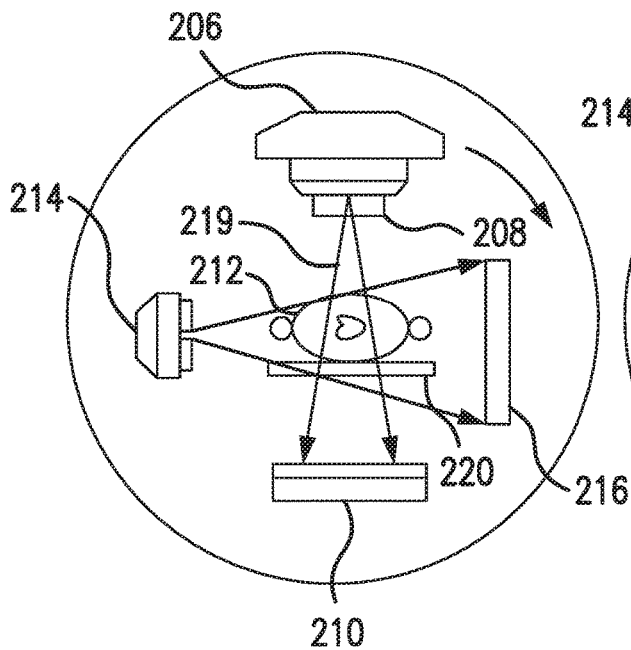
FIGS. 12C-12D illustrate an arrangement of Linac radiation treatment beam delivery integrated with kV conventional-CT/spectral-CT and SPECT imaging of the system during the treatment.
Figure 12D:
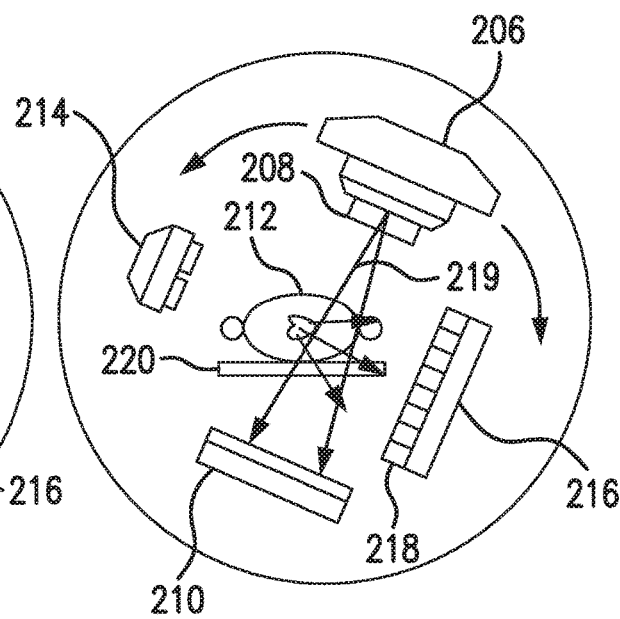

When performing radiation therapy, as shown in FIGS. 12C-12D, the MV X-ray beam from the treatment head 206 of a Linac can be tailored and intensity modulated by a MLC 208 based on the guidance of the pre-obtained diagnostic conventional-CT/spectral-CT/SPECT images of the system. The tailored narrow radiation treatment beam 219, which highly conforms to the target volume of tumors defined based on the images of tumors, irradiates the tumor within the patient 212 on the treatment couch 220 and traverses the patient 212 towards the MV X-ray imager 210. Before radiation therapy, the patient 212 can be moved to a proper position through adjusting the treatment couch 220 based on the information from the obtained images. During the radiation therapy, the radiation treatment beam 219 rotates around the tumor via rotation of the treatment head 206 and the MV X-ray imager 210, wherein both can be attached to the gantry 202 of the system 200.

During the radiation treatment beam delivery, as shown in FIG. 12C, the X-ray tube can be turned on for real-time convention-CT/spectral-CT imaging monitoring of the tumor's motion. As shown in FIG. 12D, SPECT imaging can also be performed with the radiopharmaceuticals injected into the patient 212 to visualize the changes of the tumor, so that necessary adjustment of the patient position and radiation intensity profiles could be done during the radiation treatment beam delivery based on these images.

Figure 13:
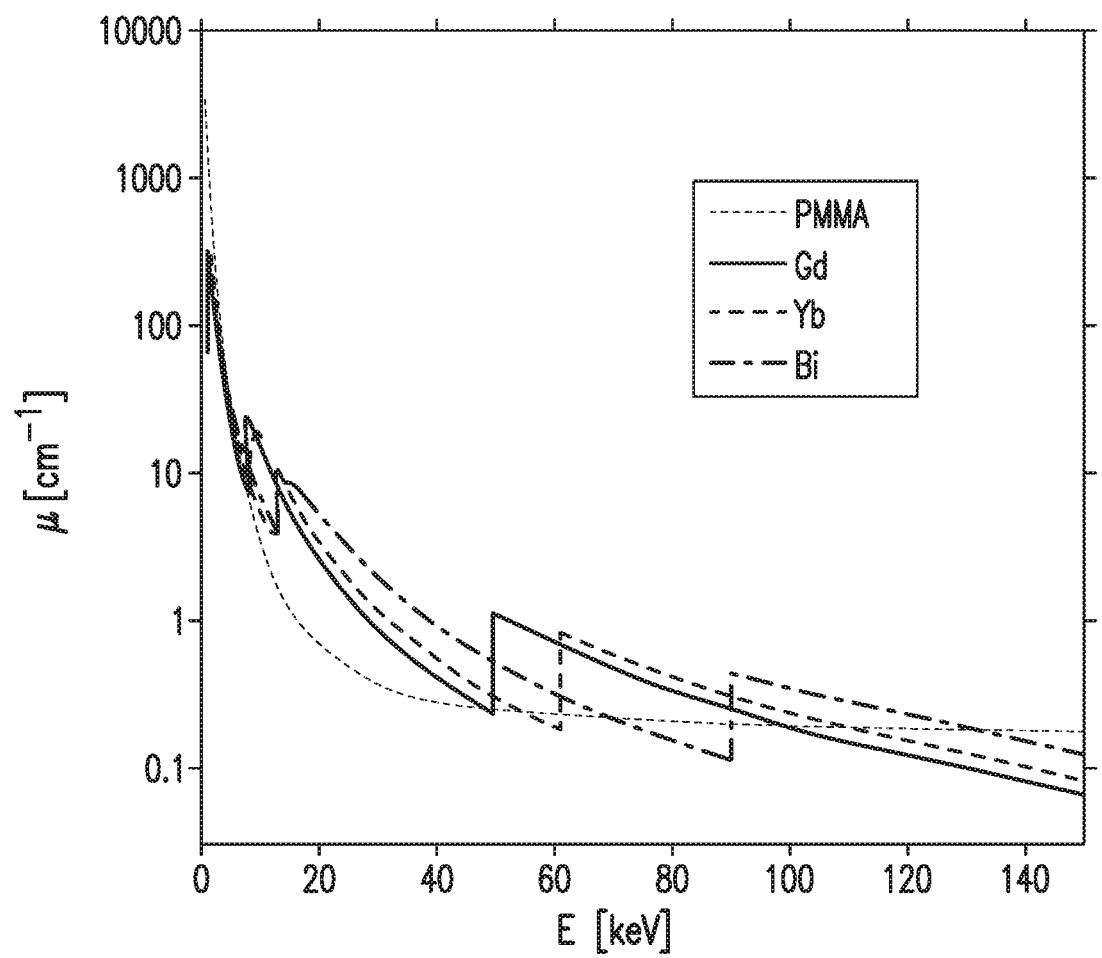
FIG. 13 explains K-edge imaging of multiple contrast elements in spectral CT imaging. The graph compares the linear attenuation coefficients of gadolinium, ytterbium, bismuth (all 60 mg/cm$^3$) and PMMA (1.195 g/cm$^3$), wherein the main K-edge absorption energies of gadolinium, ytterbium, and bismuth are 50.2, 61.3, 90.5 keV, respectively.

In exemplary aspects, in X-ray spectral CT imaging, the contrast agents, which are often composed of one or more high-atomic number elements such as iodine, gadolinium, ytterbium or bismuth, can be administrated to the patient being scanned. The K-edge discontinuities in the linear attenuation coefficients of these elements can be characteristic and unique, and can be used to discriminate these chemical elements based on their different K-edge absorption energies. As shown in FIG. 13, the graph compares the linear attenuation coefficients of gadolinium, ytterbium and bismuth (all 60 mg cm-3) and PMMA (1.195 g cm-3), wherein, the K-edge absorption energies of gadolinium, ytterbium and bismuth are 50.2, 61.3, 90.5 keV, respectively.

When polychromatic X-rays usually used clinically to traverse the subject are administered with contrast agents containing elements with K-edge absorption features, the output X-ray spectrum can contain the discontinuous energy-dependence attenuation information of the elements. By selecting proper multiple energy windows or bins corresponding to the specific elements, using the disclosed K-edge imaging method, the components in the contrast agents can be decomposed, and the distribution of these components can be imaged separately by conventional CBCT image reconstruction methods (e.g., the FDK (Feldkamp, Davis and Kress) algorithm) that use the separated spectral data relative to each element.

Because the conventional kV beam imagers operating in the integration mode can hardly realize K-edge imaging because the output of these detectors working in the integration mode weights each photon by its energy, thereby assigning more weight to higher energy photons. This weighting scheme decreases the image contrast because the contrast between materials generally depends on low-energy photons. In addition, due to the limited energy resolution capacity of these conventional kV beam imagers, new imagers with higher energy resolution are ideal.

The photon counting imagers using semiconductor materials such as CZT, cadmium telluride (CdTe) work in pulse mode. These kinds of imagers, featuring very high energy resolution, provide sufficient spectral discrimination capacity to reveal the distinct K-edge discontinuities of X-ray attenuation of the contrast elements, and can be the best choice to perform spectral-CT imaging with contrast agents. The CZT detector allows extraction of the spectral information through using K-edge and slope effects to identify elemental signatures. Moreover, because the CZT-based imagers can work at room temperature without complicated and cumbersome cooling system, the system 200 preferably uses a CZT imager considering the gantry load and rotation stability. However, it is contemplated that other detectors can be used.

The pixel size of an imager determines the intrinsic resolution of an imaging system. The disclosed system 200 facilitates human image-guided radiotherapy, so the exemplary pixel size of the CZT imager can range from about 0.5 to about 1.5 mm considering both the imaging resolution and the complexity of photon counting electronics of the CZT imager. Theoretically, each pixel records the energy of a photon hitting it as an individual current signal pulse, so the energy distribution of all the photons can be revealed through analyzing all these signal pulses. In practice, several energy bins per pixel can be used to count and classify these pulses, and the final spectral CT imaging can be reconstructed from the separated projection images of these energy bins. To avoid spectral distortion caused by pulse pile-up effect occurred at the high photon count rate case, the X-ray photon flux can be usually controlled so that the photon count rate of the CZT imager can be usually below $5 \times 10^5$ cps $mm^2$. Because it can be difficult to manufacture large area CZT detectors to suit to human size imaging application, several modules of the smaller CZT detectors can be used together as an exemplary embodiment of the disclosure.

Exemplary Methods for Radiation Therapy in the Multiple Radiation Source System

Figure 22:
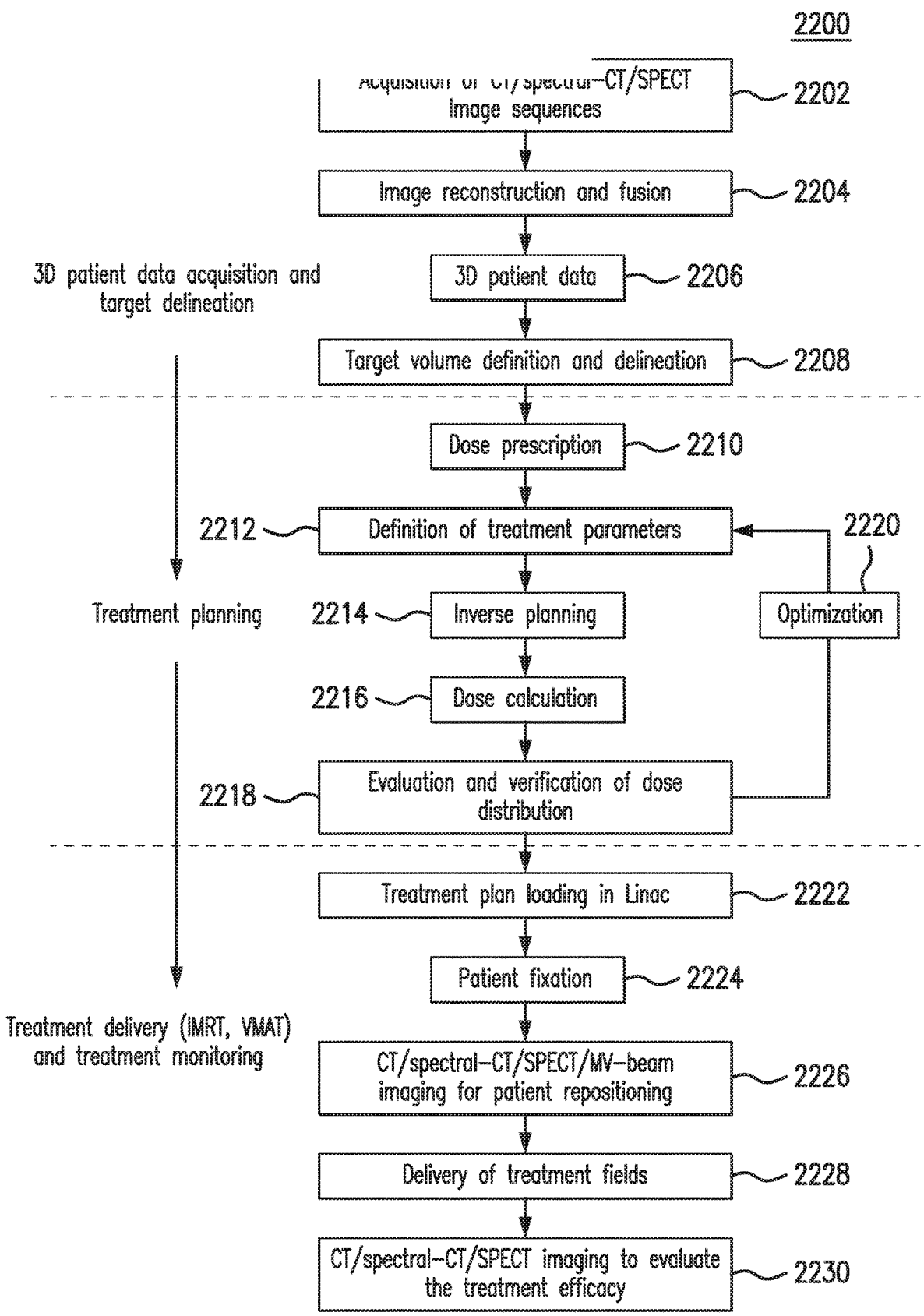
FIG. 22 is a flowchart showing a conventional-CT/spectral-CT/SPECT image-guided radiation therapy process according to an embodiment of processes based on the system in FIG. 10.

An exemplary embodiment of the process of conventional-CT/spectral-CT/SPECT image-guided radiation therapy of the system 200 is illustrated in FIG. 22. The streamlined process (2200) includes 3D patient data sets acquisition from the multiple modalities of imaging, target volume definition and delineation based on the images and oncologists' experiences, 3D treatment planning, and treatment delivery and imaging treatment efficacy during the course of radiation therapy.

After acquiring the conventional-CT, spectral-CT, and SPECT image sequences (2202), the images of a patient (e.g., human subject) can be reconstructed using the reconstruction algorithms and then fused based on the same geometry coordinates (2204). The 3D patient data sets obtained from the fused images, which reveal the anatomical structure and molecular features of the tumors within the patient, can help define the CTV of the tumors to be treated (2206). After considering the motion and shape changes of the tumors, and the uncertainties of the patient set-up and beam delivery, also based on the oncologists' experiences, the irradiation volumes of the tumors that include CTV and surrounding margins can be delineated (2208). In addition to the irradiated target volumes, the organs at risk can be defined and delineated to avoid side effects from the radiation irradiation.

After delineating the target volumes and organs at risk, dose prescription can be provided by the radiation oncologist and an optimal treatment strategy should be designed before treatment (2210). The 3D treatment planning finds the optimal treatment strategy by evaluating and optimizing of some optional strategies based on the individual 3D patient data sets. First, the treatment parameters, including the number of beams, beam modality (photons or electrons), beam energy, beam orientations, and beam profiles/beam weights, can be defined in the initial treatment plan (2212). Secondly, the dose distribution resulting from the beams is calculated using a dose calculation algorithm (2214). Thirdly, the calculated dose distribution can be evaluated qualitatively and quantitatively, wherein the dose-volume-histograms (DVHs) and 3D dose distribution fused on the CT images can be usually used to display information about the 3D dose distributions (2216). And the dose distribution can also be verified using some specific phantoms in the quality assurance process of patient's treatment plan (2218). If the plan does not meet the expected distribution and specific constraints, the treatment parameters can be modified and an iterative process is performed until an optimal plan can be found (2220). During the optimization of the treatment plan, the inverse planning can be usually included in the treatment mode of Intensity Modulated Radiation Therapy (IMRT) or Volumetric Modulated Arc Therapy (VMAT) or RapidArc® Radiotherapy.

After the optimal plan is confirmed and selected, the therapist should specify the practical applied treatment dose and fractionation scheme. Then the treatment plan can be loaded to a Linac-based radiation treatment system to perform the actual treatment beam delivery (2222). Before treatment, the patient must be fixed and immobilized to avoid position changes during the treatment (2224). The orientation and position of the patient can be also adjusted through multiple dimensional motion of the couch based on CT/spectral-CT/SPECT/MV-beam imaging (2226). The IMRT or VMAT radiation therapy technique can be used to deliver the treatment fields through using the MLC that integrated with the Linac system 200 (2228). During the treatment, the kV beam imaging, spectral-CT, SPECT and MV beam portal imaging can be optionally used to monitor the tumor or target changes, and then adjust treatment beam and/or couch position if necessary. In addition, kV beam CBCT, spectral-CT, and SPECT acquired by CZT imager during the course of radiation therapy can be used to evaluate the treatment efficacy (2230).

In exemplary aspects, it is contemplated that adjustment of the couch position can be accomplished manually or through the use of one or more actuators (e.g., electrical actuators, mechanical actuators, electro-mechanical actuators, hydraulic actuators, pneumatic actuators, and combinations thereof) that are mechanically coupled to the treatment couch and communicatively coupled to one or more processors or processor units or a computer system as further disclosed herein to permit selective control of the couch position.

Exemplary Aspects of Systems Having Multiple Radiation Sources

The following description relates to exemplary, non-limiting examples of configurations for the disclosed therapy systems.

Aspect 1: An image-guided radiation therapy system comprising: a gantry that rotates around its central axis; a radiation source (MV source) that rotates around the central axis of the gantry along a path and delivers the radiation beam towards an object on a couch; a multileaf collimator (MLC) that tailors the radiation beam from said radiation source; a megavoltage (MV) beam imager that is positioned on the opposite of said radiation source; a conventional CT system comprising: an X-ray source emitting an cone-beam X-ray beam towards said object; CZT imager receiving the X-ray photons that traverse said object, after acquiring complete projection data by rotating the X-ray source and the CZT imager around said object, the imager generating three dimensional anatomical image of the object; a spectral CT system comprising: an X-ray source emitting a cone-beam X-ray beam towards said object usually injected with contrast agents; a CZT imager receiving the X-ray photons that traverse said object, after acquiring complete projection data by rotating the X-ray source and the imager around said object, the imager generate three dimensional spectral computed tomography images using different X-ray energy bins; a SPECT system comprising: isotope-labeled radiopharmaceuticals injected into said object; a high-resolution collimator that directs gamma rays emitted from the isotope tracers perpendicularly to the surface of a gamma ray imager; a CZT imager that works in photon pulse-counting mode to receive collimated gamma rays emitted from the isotope tracers within said object, after acquiring projection data by rotating the imager around said object, the imager generating three dimensional images of isotope distribution within said object; and a workstation performing three dimensional treatment planning based on the images from conventional CT, spectral CT and SPECT imaging of said object, and connecting said radiation source and said conventional CT, spectral CT and SPECT imaging systems, wherein, said treatment planning is performed by controlling said radiation source and positions of said object.

Aspect 2: The system of aspect 1, wherein the X-ray source for conventional CT imaging and the X-ray source for spectral CT imaging are a single X-ray source that emits X-ray beams at a diagnostic energy level.

Aspect 3: The system of aspect 2, wherein the single X-ray source is a kV beam X-ray source.

Aspect 4: The system of aspect 1, wherein the conventional CT, spectral CT and SPECT triple imaging modalities share the same CZT imager.

Aspect 5: The system of aspect 4, wherein the CZT imager is a pixelated CZT flat panel imager.

Aspect 6: The system of aspect 4, wherein the CZT imager is configured to work in an integration mode when the CZT imager is used during conventional CT imaging.

Aspect 7: The system of aspect 4, the CZT imager is configured to work in a photon pulse-counting mode when the CZT imager is used during conventional CT imaging, and wherein the CZT imager is configured to use a single energy bin is used to detect an entire spectral range of the detected photons.

Aspect 8: The system of aspect 4, wherein the CZT imager is configured to work in a photo pulse-counting mode when the CZT imager is used during spectral CT and SPECT imaging, and wherein the CZT imager is configured to apply a plurality of energy bins to each resulting pixel.

Aspect 9: The system of aspect 1, wherein the high-resolution collimator comprises a parallel square-hole collimator.

Aspect 10: The system of aspect 9, wherein the holes of the collimator have a hole size that matches the pixel size of the pixelated CZT flat panel imager.

Aspect 11: The system of aspect 1, wherein the X-ray source and the CZT imager are attached to the gantry.

Aspect 12: The system of aspect 11, wherein the X-ray source and the CZT imager are provided in a kV cone-beam computed tomography (CBCT) configuration.

Aspect 13: The system of aspect 11, wherein the X-ray source and the CZT imager both rotate around the central axis of the gantry.

Aspect 14: The system of aspect 11, wherein the relative distance between the X-ray source and the CZT imager is adjustable by translating the X-ray source and the CZT imager relative to a radial line extending perpendicularly to the central axis of the gantry.

Aspect 15: The system of aspect 1, wherein the radiation source is a linear accelerator (Linac).

Aspect 16: The system of aspect 1, wherein the radiation source and the MV beam imager are provided in a MV CBCT configuration.

Aspect 17: The system of aspect 16, wherein the MV CBCT is orthorhombic to the KV CBCT.

Aspect 18: The system of aspect 1, wherein the MLC is positioned in front of the radiation source to change the shapes and intensity profiles of the radiation treatment beams that are delivered to the object.

Aspect 19: The system of aspect 1, further comprising a couch, wherein the couch is positioned in a central portion of the MV CBCT and KV CBCT by a plurality of dimensional electronic positioners.

Aspect 20: The system of aspect 1, wherein the contrast agents injected into the object comprise one or more high atomic number chemical elements, such as gadolinium, ytterbium, bismuth, gold, and the like.

Aspect 21: The system of aspect 1, wherein the targeted radiopharmaceuticals injected into the object comprise one or more types of isotopes, such as $^{99m}$Tc, $^{123}$I and the like.

Aspect 22: A method for image-guided radiation therapy comprising: rotating the radiation source attached to the gantry along an accurate path to deliver treatment beam to an object; tailoring the treatment beams towards said object from said radiation source using a MLC; using a MV imager to detect the radiation treatment beam; using a kV X-ray source for conventional CT imaging and spectral CT imaging; using a single photon counting CZT flat-panel imager to detect X-ray photons from said X-ray source and gamma ray photons from the isotope-labeled radiopharmaceuticals injected into said object; generating three dimensional images of said object, wherein the images are fused images from spectral CT images, SPECT images and conventional CT images of the same said object; connecting said radiation treatment beam delivery and said conventional CT, spectral CT and SPECT triple imaging of said object, wherein the treatment beam delivery is guided by the triple imaging of said object.

Aspect 23: The method of aspect 22, wherein said radiation source is a Linac.

Aspect 24: The method of aspect 22, wherein said radiation source and said MV imager form a MV CBCT, and said X-ray source and said single photon counting imager form a kV CBCT, where the MV CBCT and the kV CBCT are orthogonal (oriented perpendicularly) to each other.

Aspect 25: The method of aspect 22, further comprising three dimensional treatment panning based on the guidance of said triple imaging of said object.

Aspect 26: The method of aspect 22, wherein the treatment beams or fields can be delivered by Intensity-Modulated Radiation Therapy (IMRT) or Volumetric Modulated Arc Therapy (VMRT) radiation therapy technique through the MLC attached to said radiation source.

Aspect 27: The method of aspect 22, further comprising adjusting said treatment beams during the treatment based on said triple imaging monitoring of said object.

Aspect 28: The method of aspect 22, further comprising adjusting the position of said couch during the treatment based on said triple imaging monitoring of said object.

Aspect 29: The method of aspect 22, wherein the photon counting flat-panel imager is a CZT imager.

Aspect 30: A radiotherapy system comprising: a first radiation source that is configured to emit a first radiation beam for imaging a subject; a first imager that is positioned opposite the first radiation source to detect the first radiation beam after the first radiation beam has traversed the subject, wherein the first imager is configured to detect plurality of different types of images of the subject; a second radiation source that is configured to emit a second radiation beam to provide radiotherapy to the subject; a second imager that is positioned opposite the second radiation source to detect the second radiation beam after the second radiation beam has traversed the subject; and a computer system that is programmed to: combine the types of images of the subject into a comprehensive image of the subject; identify one or more target areas within the subject for treatment based, at least in part, on the comprehensive image of the subject; determine one or more treatment characteristics for the one or more target areas based, at least in part, on the comprehensive image of the subject and the one or more target areas; and control delivery of the radiotherapy treatment by the second radiation source to the one or more target areas within the subject according to the one or more treatment characteristics.

Aspect 31: The radiotherapy system of aspect 30, wherein the first imager is configured to produce a conventional CT image type and a spectral-CT image type, and a SPECT image type.

Aspect 32: The radiotherapy system of aspect 30, further comprising: a first collimator that is positioned between the first imager and the subject, and that is configured to direct one or more types of radiation from the subject to the first imager.

Aspect 33: The radiotherapy system of aspect 32, wherein: the one or more types of radiation comprise gamma rays, and the first imager is configured to detect the gamma rays.

Aspect 34: The radiotherapy system of aspect 32, wherein the first collimator comprises a high resolution collimator with one or more surfaces defining holes that are specifically sized or shaped.

Aspect 35: The radiotherapy system of aspect 34, wherein the holes are sized to correspond to the size of pixels in the imager.

Aspect 36: The radiotherapy system of aspect 34, wherein the high resolution collimator comprises a parallel square hole collimator.

Aspect 37: The radiotherapy system of aspect 30, wherein the first imager comprises a photon counting imager that is configured to receive photons from a radiation beam that has traversed the subject.

Aspect 38: The radiotherapy system of aspect 37, wherein the photon counting imager comprises a cadmium zinc telluride (CZT) imager.

Aspect 39: The radiotherapy system of aspect 30, wherein the first radiation source comprises an x-ray radiation source and the first radiation beam comprises an x-ray beam.

Aspect 40: The radiotherapy system of aspect 39, wherein the x-ray radiation source comprises an x-ray tube.

Aspect 41: The radiotherapy system of aspect 39, wherein the first radiation source is configured to emit the first radiation beam at a plurality of low energy levels for imaging the subject and the second radiation source is configured to emit the second radiation at a high energy level that is higher than the low energy levels of the first radiation beam to provide the radiotherapy to the subject.

Aspect 42: The radiotherapy system of aspect 41, wherein the plurality of low energy levels range from about 70 kVp to about 150 kVp.

Aspect 43: The radiotherapy system of aspect 41, wherein the high energy level ranges from about 6 MV to about 10 MV.

Aspect 44: The radiotherapy system of aspect 30, wherein the first imager detects the plurality of different types of images of the subject in advance of the radiotherapy treatment being delivered to the subject.

Aspect 45: The radiotherapy system of aspect 30, wherein: the second imager detects port images of the subject while the radiotherapy treatment is being delivered to the subject, and the computer system is programmed to repeatedly perform the combining, the identifying, the determining, and the controlling on while the radiotherapy treatment is being delivered.

Aspect 46: The radiotherapy system of aspect 30, further comprising: a gantry that is rotatable about a central axis, wherein the first radiation source, the first imager, the second radiation source, and the second imager are mounted to the gantry, and wherein the computer system is further programmed to control rotation of the gantry according to the one or more treatment characteristics.

Aspect 47: The radiotherapy system of aspect 30, wherein the first imager comprises a CZT imager.

Aspect 48: The radiotherapy system of aspect 30, further comprising: a moveable support structure configured to support the subject in a desired orientation relative to the first and second radiation sources, wherein the computer system is further programmed to control movement of the moveable support structure.

Systems Having a Single Radiation Source

Figure 2A:
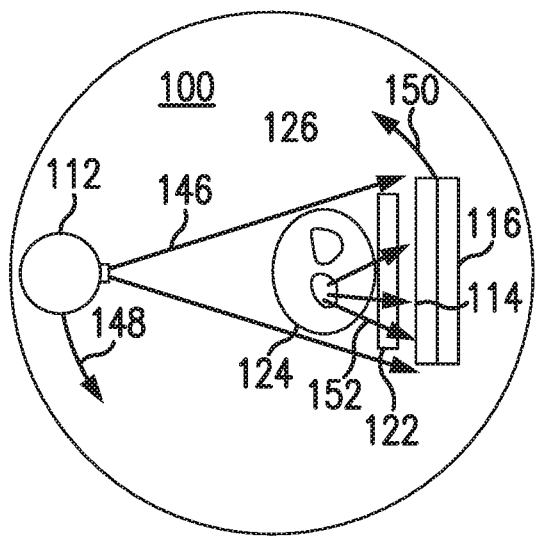
FIGS. 2A-2D depict longitudinal views of the example radiation therapy system in use mobile computing devices.
Figure 2B:
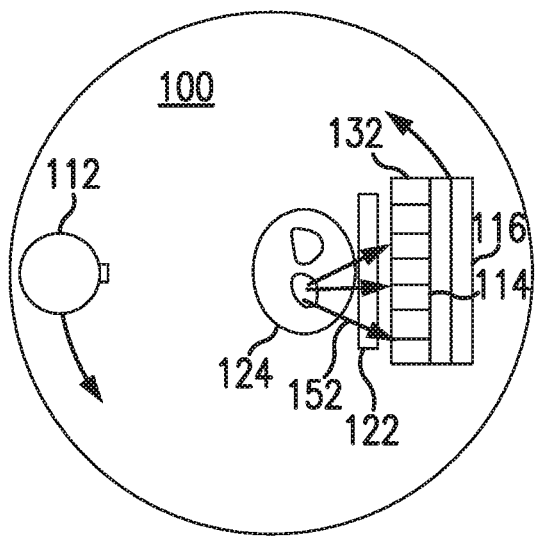
Figure 2C:
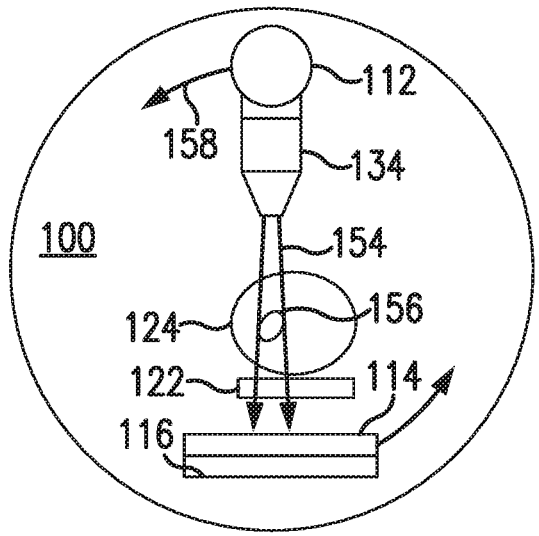
Figure 2D:
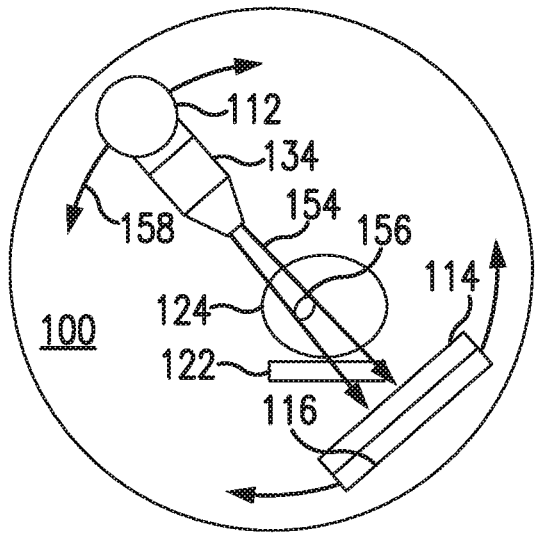

In exemplary aspects, and with reference to FIGS. 1-2D, the at least one radiation source of the system can comprise a single radiation source, and the at least one imager can comprise a single imager. In these aspects, it is contemplated that the imager can be oriented toward the radiation source, with the radiation source being positioned on an opposing side of the subject from the imager. In exemplary aspects, and as further disclosed herein, systems comprising a single radiation source and a single imager can be used to image and provide therapy to small animal subjects.

FIG. 1 depicts a side view of an example radiation therapy system 100 that uses multiple combined imaging techniques to guide radiation therapy treatment for a smaller subject 124, such as a small animal. In this aspect of the disclosure, there is a single radiation source and a single imager. The example system 100 can use any of a variety of appropriate imaging combinations, such as combinations of conventional CT, spectral CT, and SPECT imaging. For example, the system 100 can include an imaging unit that combines conventional-CT, spectral-CT, and SPECT imaging. The system 100 can also include a radiation treatment unit (e.g., x-ray beam radiation unit) that uses the same radiation source (e.g., x-ray source) and the same imager as the imaging unit. By using common radiation and imaging sources, the resulting images (e.g., combined conventional-CT/spectral-CT/SPECT images) can be properly aligned with the radiation source, which can allow for more precision with the deployment of radiation therapy.

As depicted, the example system 100 includes a radiation source 112, which in this example can be an x-ray tube 112 with an appropriate energy range, such as between about 50 kVp and 250 kVp. Other types of radiation sources and/or energy ranges can also be possible. Optionally, in use, the radiation source 112 can be configured to emit radiation in a first range of energy levels for diagnostic applications and a second range of energy levels for treatment applications. In these aspects, it is contemplated that the first range of energy levels can range from about 50 kVp to about 120 kVp, while the second range of energy levels can range from about 150 kVp to about 300 kVp.

The system 100 also includes an imager 114 that can be located between the radiation source 112 and radiation shielding 116 (e.g., lead shielding plate). The imager 114 can be any of a variety of appropriate imagers, such as a pixelated CZT imager and/or other appropriate semiconductor radiation imagers. The radiation source 112 and the imager 114 can both be attached to a rotation gantry 118 that rotates around a central axis 120.

The system 100 also includes a subject support 122, such as a horizontal support couch, which can support a subject 124, such as a small animal (e.g., mouse, rat). The subject 124 can be administered with one or more contrast agents and/or radioisotope labeled pharmaceuticals, which can be scanned and recorded when provided to the subject 124. The position of the support 122 can be controlled by, for example, a 3D electronic linear translated stage 126. The radiation source 112 and the imager 114 can translate along radial tracks 128 and 130 relative to the rotation center axis 120 of the gantry 118, respectively. The track 128 and 130 can extend along parallel radial planes relative to the central axis 120, which allows the axis of the radiation beam from the radiation source 112 to remain perpendicular to the imager 114.

For SPECT imaging, the system 100 can use a dedicated high resolution parallel-hole collimator 132 that can be positioned between the subject 124 and the imager 114 so that gamma rays emitted from the subject 124 can be collimated before passing to the imager 114. The collimator 132 can be made out of any of a variety of appropriate materials, such as lead, and can be positioned so that it overlays and can be adjacent to imager 114. A set of radiation collimators 134 (e.g., x-ray collimators, multileaf-collimators) can be attached to the head of the radiation source 112 to tailor the output beam for irradiation of one or more target locations on the subject 124. The imager 114 can simultaneously detect x-ray photons from the radiation source 112 and gamma photons emitted from an isotopic radiation source that was previously administered to and can be located within the subject 124.

A radiation shielded protective enclosure 136 can cover and enclose the gantry 118 and the stage 126. The enclosure 136 can be located and used on any appropriate surface, such as a bench 138. Movement of the gantry 118 and the stage 126 can be controlled and driven by motion controllers 140, which can send electrical control signals to the gantry 118 and the stage 126 based on controls from, for example, a work station 142 (e.g., computing device). It is contemplated that the gantry 118 can comprise one or more actuators (e.g., electrical actuators, mechanical actuators, electro-mechanical actuators, hydraulic actuators, pneumatic actuators, and combinations thereof) that are configured to effect desired movement of selected portions of the gantry 118 in response to the electrical control signals. The work station 142 can also interface with and control a high voltage controller 144 that supplies power to the radiation source 112.

FIGS. 2A-D depict longitudinal views of the example radiation therapy system 100 in use. Referring to FIG. 2A, with the subject 124 having been injected with contrast agents containing, for example, one or more high atomic number elements and/or materials before image acquisition, the radiation source 112 can be turned on with a low energy level (e.g., less than 140 kVp), and a radiation beam 146 (e.g., x-ray beam) traverses the subject 124 towards the imager 114. A projection image can be obtained by the imager 114 by counting photons that interact with each pixel. The energy and position of each photon can be recorded by the read-out electronics of the imager 114. The radiation source 112 and the imager 114 can rotate synchronically along the circle tracks 148 and 150, respectively, to perform full 360° scanning of the subject 124. Projection data can be obtained by the imager 114 along the entire 360° scan and can be transferred to the workstation 142, which can either alone or in communication with other computing devices (e.g., remote server system, cloud system, distributed computing system) process and generate tomographic images of the subject 124. If a radionuclide labeled pharmaceutical was additionally and/or alternatively injected into the subject 124, gamma rays 152 can be emitted from the subject 124 that can also be record by the imager 114. The imager 114 can be selected to have a sufficiently high energy resolution so that it can be able to readily and accurately separate the gamma rays 152 from the x-rays 146 based on their energy differences. An example of such an imager can be a CZT imager. Other imagers, such as CdTe imagers, can also be used. The system 100 can acquire conventional CT images and spectral CT images with the imager 114. The acquisition process for spectral CT imaging can be the same as for conventional CT imaging, except that the imager 114 can average the whole spectral range of the x-ray photons for conventional CT imaging.

Referring to FIG. 2B, the system 100 can acquire SPECT images through the use of one or more radioisotope labeled radiopharmaceuticals that can be administered to the subject 124 before image acquisition. SPECT images can be obtained, for example, while the radiation source 112 can be turned off (not emitting radiation). The radiopharmaceuticals can aggregate to local regions of interest within the subject 124 and can cause isotropic emission of gamma rays 152 from the radiopharmaceuticals within the subject 124, which the collimator 132 can collimate before being detected by the imager 114. The collimator 132 can be placed in front of the imager 114 to collimate the gamma rays 152 normally directed to the surface of the imager 114 pixels. Any of a variety of appropriate types of collimators can be used that can be capable of collimating radiation, such as parallel-hole collimators, where the holes of the collimator 132 can be designed to match the size of the pixel of the imager 114, which can allow for spatial resolution images to be obtained. Other shaped collimators (e.g., pinhole collimators) can also be used. Data collected by the imager 114 from the projections can be transferred to the workstation 142 to generate tomographic images (e.g., SPECT images) that reveal the radiopharmaceutical distribution with the subject 124. In some implementations, when the imager 114 can be an imager that has improved energy resolution (e.g., CZT imagers or CdTe imagers) as compared with conventional imagers (e.g., conventional NaI imagers), radiopharmaceuticals with two or more isotopes can be imaged simultaneously by the imager 114 even if the photopeaks of these isotopes can be very close to each other, such as $^{99m}$Tc (140 keV) and $^{123}$I (160 keV).

Referring to FIGS. 2C-D, these figures depict examples of performing radiation therapy when the radiation source 112 can be turned on with a high energy level (e.g., between about 200 kVp to 250 kVp). In the depicted examples, the collimator 134 attached to the radiation source 112 can supply shaped radiation fields (e.g., circular-shaped radiation field, square-shaped radiation field) that can be changeable and have particularly dimensioned field sizes at the treatment site (e.g., about 1 to 20 mm in diameter at treatment site). The collimated treatment beam 154 irradiates the previously positioned target 156 (e.g., tumor, lesion) in the subject 124 towards the imager 114, and the imager 114 records a projection image of the treatment beam 154 that traverses the target 156 within the source 124. To reduce the radiation dose deposition in surrounding healthy tissues, while ensure sufficient radiation dose to the target 156 within the subject 124, the treatment beam 154 rotates along a path 158 around the target 156 to deliver the radiation dose (e.g., Intensity-Modulated Radiation Therapy (IMRT), Volumetric Modulated Arc Therapy (VMAT)). It should be noted that the position and geometry of the target 156 can be derived from the previously obtained conventional-CT, spectral-CT, and SPECT images, as described above with regard to FIGS. 2A-B. In addition, the projection images of the treatment beam 154 through the subject 124 obtained by imager 114 during the treatment can also be used to guide the positioning and motion of the beam 154, which can improve the precision of the radiation therapy being delivered.

Computer Subsystems

Figure 20:
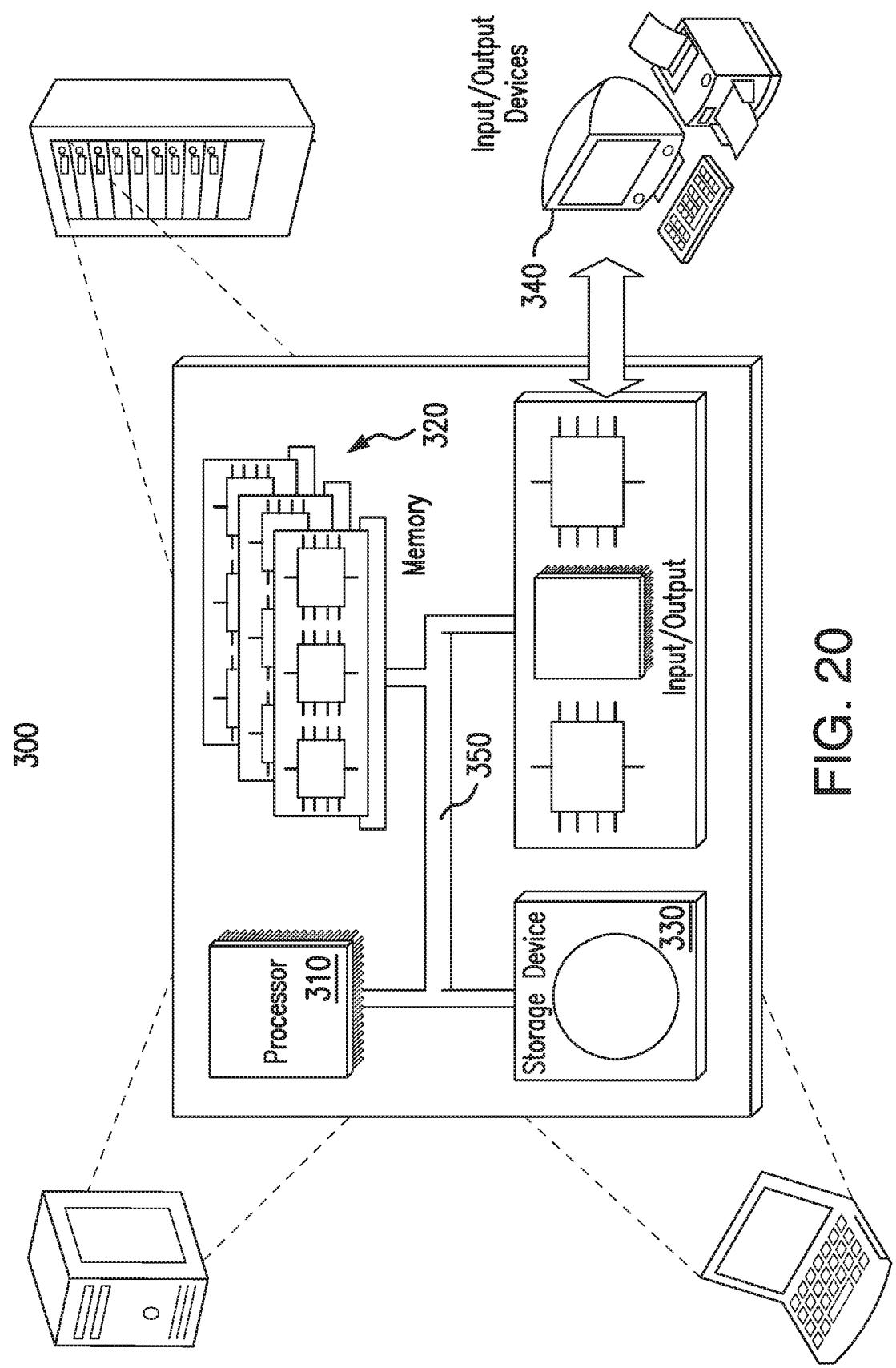
FIG. 20 illustrates a schematic diagram of an exemplary generic computer system applicable to a small animal embodiment or human configured embodiment.

FIG. 20 illustrates a schematic diagram of an exemplary computer subsystem 300 for use with any of systems 100 or 200. The system 300 can be used for the operations described in association with the systems, processes, and techniques described throughout this document, such as part of the treatment systems 100, 200 and/or to implement the respect techniques for each configuration 100 and 200. For example, the computing system 300 can be a subsystem within the systems 100 and 200. The computing system 300 can be programmed to perform the image-based operations and determinations further described herein.

The subsystem 300 includes a processor 310, a memory 320, a storage device 330, and an input/output device 340. Each of the components 310, 320, 330, and 320 can be interconnected using a system bus 350. The processor 310 is capable of processing instructions for execution within the system 300. In one implementation, the processor 310 can be a single-threaded processor. In another implementation, the processor 310 can be a multi-threaded processor. The processor 310 can be capable of processing instructions stored in the memory 320 or on the storage device 330 to display graphical information for a user interface on the input/output device 340.

The memory 320 stores information within the system 300. In one implementation, the memory 320 can be a computer-readable medium. In one implementation, the memory 320 can be a volatile memory unit. In another implementation, the memory 320 can be a non-volatile memory unit.

The storage device 330 can be capable of providing mass storage for the system 300. In one implementation, the storage device 330 can be a computer-readable medium. In various different implementations, the storage device 330 may be a floppy disk device, a hard disk device, an optical disk device, or a tape device.

The input/output device 340 provides input/output operations for the system 300. In one implementation, the input/output device 340 includes a keyboard and/or pointing device. In another implementation, the input/output device 340 includes a display unit for displaying graphical user interfaces.

Embodiments of the subject matter, the functional operations and the processes described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that can be generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that can be located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can be based on general or special purpose microprocessors or both, or any other kind of central processing unit. Generally, a central processing unit will receive instructions and data from a read-only memory or a random access memory or both. The essential elements of a computer can be a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that can be used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server can be generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that can be described in this specification in the context of separate embodiments can also be implemented in combination in a single embodiment. Conversely, various features that can be described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Exemplary Methods for Radiation Therapy in the Single Radiation Source System

Figure 21:
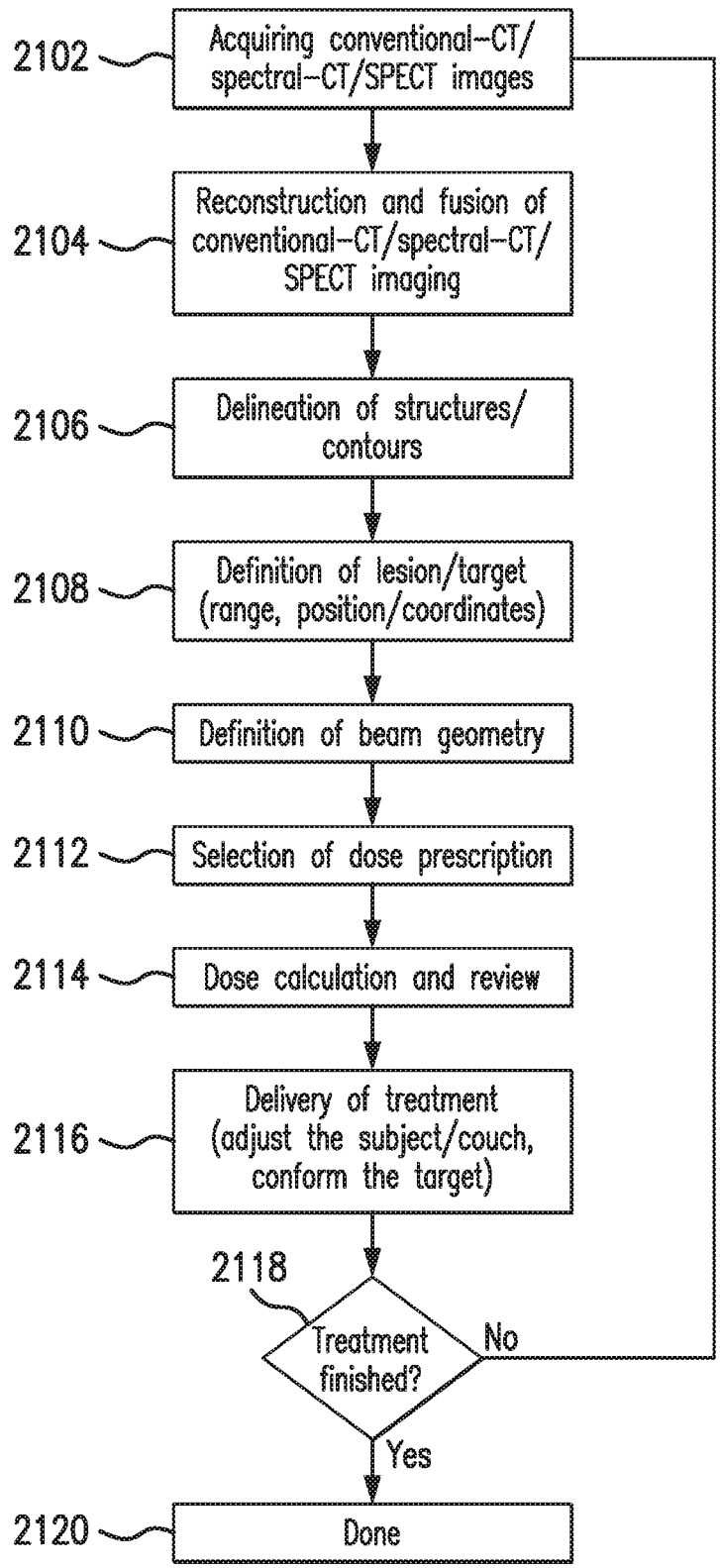
FIG. 21 is a flowchart of an example technique for performing image guided radiation therapy.

FIG. 21 is a flowchart of an example technique 2100 for performing image guided radiation therapy. The example technique 2100 can be performed by any of a variety of appropriate systems, such as the system 100 disclosed herein, and can use a combination of multiple types of imaging (e.g., combination of conventional-CT, spectral-CT, and SPECT) to provide image-guided radiation therapy. The example technique 2100 can include, for example, precise localization of lesion or target volume, beam definition, selection of dose prescription, dose review, delivery of designed treatment beam, and/or treatment beam adjusting during the radiation therapy.

Images can be acquired using conventional-CT, spectral CT, and SPECT imaging techniques (2102). For example, the system 100 can acquire conventional CT and spectral CT images of the subject 124 using the radiation source 112 and imager 114, which can rotate around the subject 124 as part of the gantry 118 to obtain full 360° scanning of the subject 124. In another example, the system 100 can acquire SPECT images of the subject 124 using the collimator 132 and the imager 114, which may also rotate around the subject 124 as part of the gantry 118.

The projection data and images can be reconstructed using one or more reconstruction algorithms and can then be combined into one image based on the same geometry coordinates (2104). Since the images can be generated using the same imager 114, which can allow the images of the subject 124 to have the same or similar coordinates, vantage point, and/or scale so that they can be readily and accurately combined.

The combined image can be used to identify the anatomical structure, chemical compositions, and the molecular features of the tissue in a subject (2106), such as, for example and without limitation, a small animal. The information from the combined image can allow the contours of different organs and definition of tumor or lesion volume in the organs to be accurately delineated (2108). For example, the range and central coordinates of tumors, lesions, and/or other items of interest within a subject can be determined. Any of a variety of appropriate image processing algorithms can be used to detect such features from the combined image. Using this information (e.g., identified structures, compositions, molecular structures, information on the location and contours of organs, tumors, and lesions), appropriate beam geometries can be determined for treating tumors and/or lesions within the subject (2110). Beam geometries can include, for example, a beam direction, beam shape, and/or beam size can be selected for treatment of the specifically sized and located lesions/tumors within the subject. The information derived from the combined image can also be used to determine the appropriate dose prescription for treating the lesions/tumors (2112). For example, the system 100 can determine the type and radiation response characteristics of the lesion as well as the radiation tolerance of surrounding tissues and, based at least in part on those details, the system 100 can determine the proper dose prescription for treatment planning. Such a dose prescription can be selected so as to provide sufficient dose to the lesion while sparing the critical normal structures from excessive irradiation.

As a safety check and to ensure correct dose delivery, the dose distribution in the lesion can be verified to conform to the dose prescription through dose calculation and dose review (2114). The system 100 can use any of a variety of appropriate algorithms to determine dose calculations, such as the Monte Carlo method. For example, the system 100 can calculate the isodose curve and/or dose-volume histogram (DVH) to analyze the dose distribution in the target. In some implementations, an inverse planning can be optionally used to optimize the parameters of the delivered beam.

With the dose distribution determined, the beam information can be used to automatically and/or manually control the position of the couch and the rotation of radiation beam for treatment (2116). For example, system 100 can be programmed to automatically determine the positioning of the stage 126 and the rotation of the gantry 118 to provide treatment to the subject 124 that can be specifically designed for the lesions and/or tumors detected within the subject 124 using the same radiation source 112 that can provide the treatment. In another example, the system 100 can provide the beam information to the workstation 142, which can allow a technician to verify, monitor, and/or control the treatment application to the subject 124. The system 100 can allow for single or multiple fractionated irradiation treatment studies in various subjects, such as small animals, and also supports drug-radiation synergy studies in a subject based on its anatomical, chemical, and/or molecular imaging capacity for monitoring and evaluating the effectiveness of the treatment. Various other uses are also possible.

A determination can be made as to whether the treatment has finished for the subject (124). If the treatment is finished, then the technique 2100 can end. If the treatment is not finished, then one or more of the steps 2102-2116 can be repeated. For example, the steps 2102-2116 can be iteratively repeated for each lesion and/or tumor that is detected within the subject. In another example, the steps 2102-2116 can be repeated for one or more lesions/tumors, with each iteration including partial treatment of the tumor/lesion followed by evaluation of the treatment on the tumor/lesion before continuing with the remainder of the treatment. In some implementations, one or more of the steps 2102-2116 can be performed in real time with the treatment delivery step 2116. For example, the steps 2102-2114 may be repeatedly performed while the treatment is being delivered at step 2116 so as to guide and verify the treatment of the subject in real time.

Although relative simple beam irradiation is described here, the system 100 can further include a conformal radiation therapy technique, such as IMRT and/or VMAT that can be used in clinical human radiation therapy through the use of a micro multi-leaf collimator in front of x-ray source.

EXPERIMENTAL EXAMPLES

The following experimental examples are exemplary, non-limiting descriptions of various exemplary features of the disclosed systems 100, 200.

Figure 14:
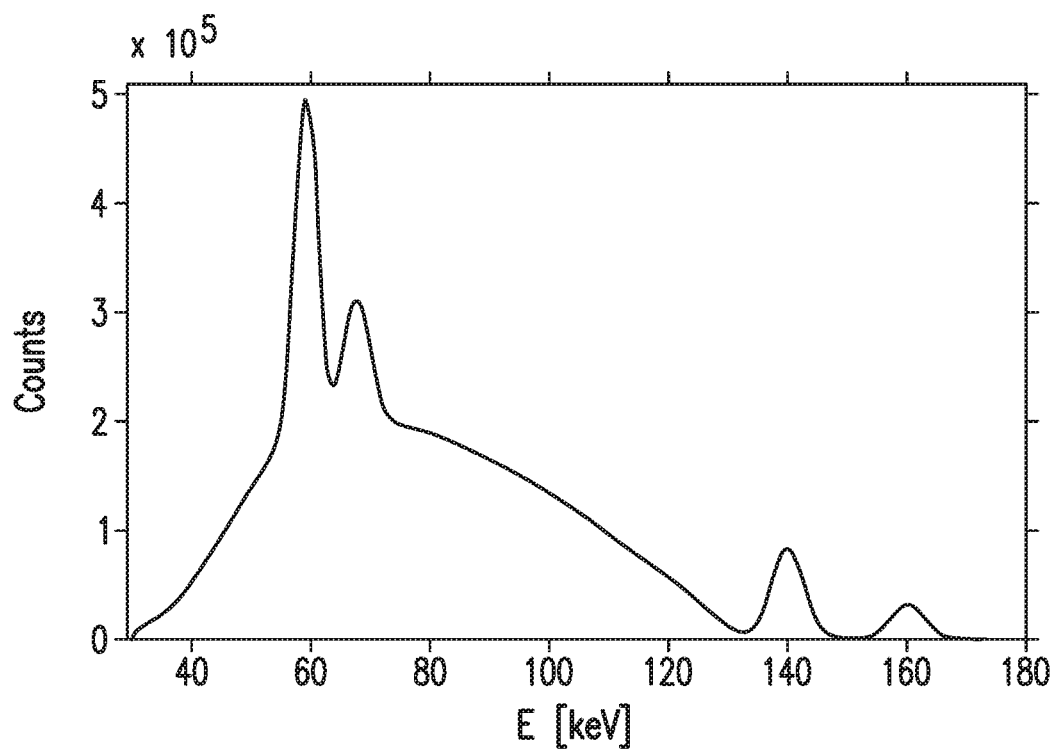
FIG. 14 shows a simulated detection of energy spectrum of 130 kVp diagnostic X-ray photons, 140 keV gamma photons from $^{99m}$Tc, and 160 keV gamma photons from $^{123}$I by a CZT imager.
Figure 15:
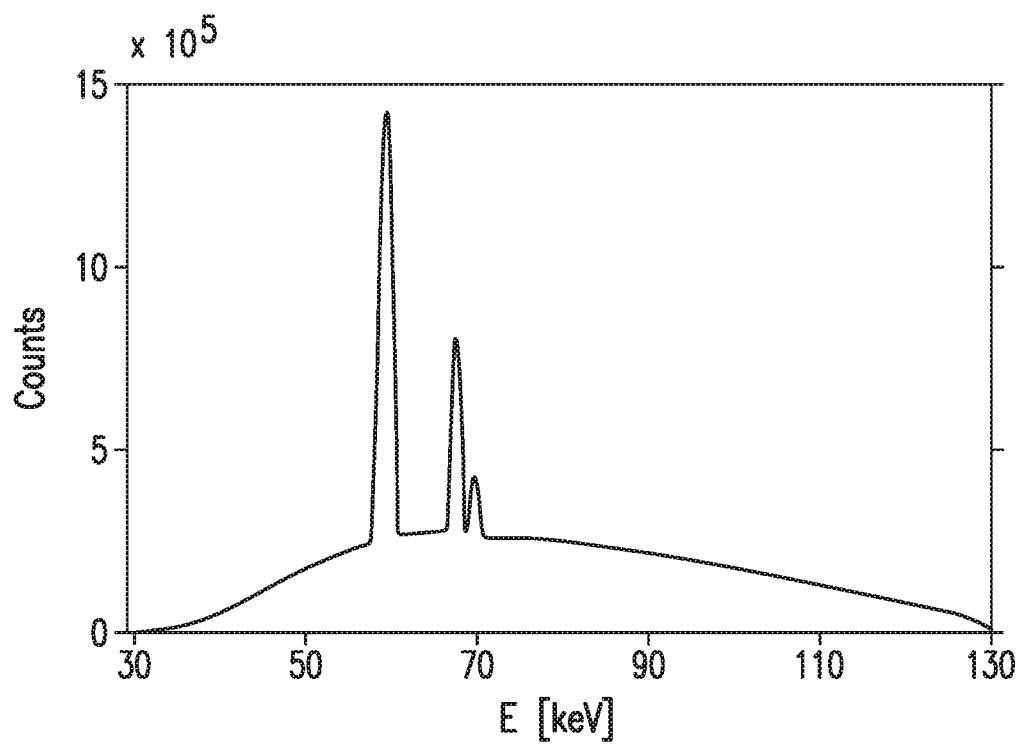
FIG. 15 shows the calculated spectral distribution of the 130 kVp X-ray beam used for Monte Carlo simulation using a SpekCalc software. The photons can be generated at 130 kVp with 4 mm Al and 0.4 mm Cu filtration and with 100 cm water in the beam.

Experimental Analysis to Determine Diagnostic and Treatment Parameters for a Multiple Radiation Source System To illustrate the performance of a CZT imager, the detection of low energy diagnostic X-ray photons and gamma photons from two types of isotopes was simulated using GATE Monte Carlo software. As shown in FIG. 14, the spectrum obtained by a pixelated CZT imager included the photopeaks of 140 keV and 160 keV, which were from the isotope $^{99m}$Tc and $^{123}$I, respectively, and also included a detected X-ray spectrum from an X-ray source at energy of 130 kV. From the detected spectrum, it can be effortless to distinguish the gamma photons from the X-ray photons; furthermore, the two different photopeaks can be identified clearly even if they are very close due to the high energy resolution ability of the CZT detector. The X-ray spectrum used for the simulation can be showed in FIG. 15, which was produced by the SpekCalc program, wherein the X-ray photons were generated at 130 kVp tube voltage with 4 mm Al and 0.4 mm Cu filtration and with 200 cm water in the beam.

As shown in FIGS. 16A-16C, several phantoms were simulated to investigate the image guidance capacity of an exemplary embodiment of the disclosed system 200. To investigate spectral CT imaging of the system to discriminate different concentrations of the same contrast agent at the same K-edge energy bin, a cylindrical PMMA phantom with four groups of inserts filled with four different concentrations of ytterbium contained aqueous solution was simulated for imaging (FIG. 16A). The four concentrations of ytterbium inserts were 20, 30, 40, and 50 mg ml$^{-1}$, respectively. The selected energy bin was 62 to 76 keV, which can be based on the optimal energy bins of K-edge image according to the previous studies.

To investigate SPECT imaging of the system to identify two different types of isotopes with different activity distributions, a cylindrical PMMA phantom with four inserts was simulated for imaging. The four inserts were filled with aqueous solution containing isotopes of $^{99m}$Tc (9 μCi ml$^{-1}$), $^{99m}$Tc (7 μCi ml$^{-1}$), $^{123}$I (9 μCi ml$^{-1}$) and $^{123}$I (7 μCi ml$^{-1}$), respectively. To reduce image blurring caused by the photons from scattering, an energy threshold was set to the detected photons.

To demonstrate the performance of combined conventional-CT/spectral-CT/SPECT triple imaging of the inventive system, as shown in FIG. 16C, a cylindrical PMMA phantom with four inserts was simulated for imaging. The four inserts were filled with aqueous solution containing element of gadolinium (30 mg ml$^{-1}$), ytterbium (30 mg ml$^{-1}$), bismuth (30 mg ml$^{-1}$), and a radiation source from $^{99m}$Tc (9 µCi ml$^{-1}$), respectively.

The disclosed system 200 can be designed for human image-guided radiotherapy; however, to speed up the process of Monte Carlo simulation, relatively small scales of phantoms and the CZT imager were designed, which did not affect the performance results of the system significantly. In the simulation of the system 200 for imaging, a kV X-ray focus to central axis of rotation distance of 400 mm and a kV X-ray focus to imager distance of 465 mm were designed, and a pixelated CZT photon counting imager with thickness of 5 mm was modeled. The imager had a 128×128 array of pixels, a pixel pitch of 0.6×0.6 mm$^2$ and the size of 76.8× 76.8 mm$^2$. A high-resolution lead collimator with parallel quadrate holes was designed to match the CZT imager for SPECT imaging. It had a length of 20 mm, a hole width of 1.2 mm and a septa width of 0.1 mm. To acquire SPECT data, a 2×2 bin to the CZT imager pixels was used to obtain high detective sensitivity. As mentioned above, the cylindrical PMMA phantoms with a diameter of 40 mm filled with different inserts were used to demonstrate the imaging performance of the system. It should be noted that the pulse pile-up effect and the charge sharing effect in the photon counting CZT imager were not considered in the simulation.

Figure 17A:
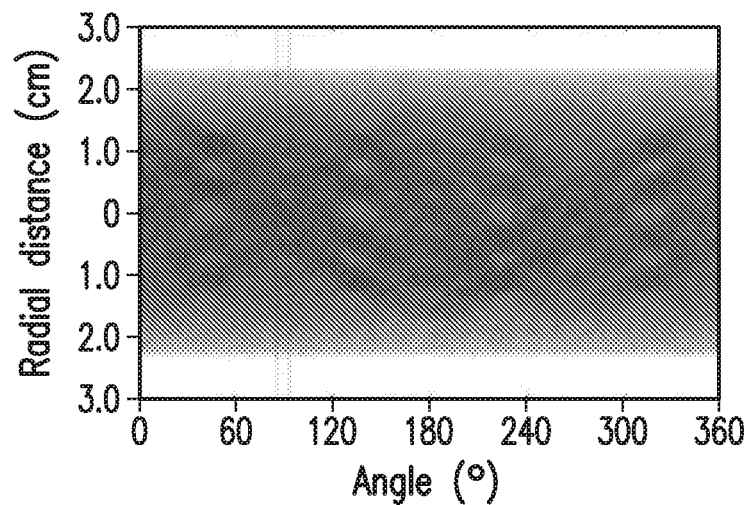
FIGS. 17A-17C show the simulated detection and reconstruction results of the four groups of ytterbium inserts with different concentrations shown in FIG. 16A.
Figure 17B:
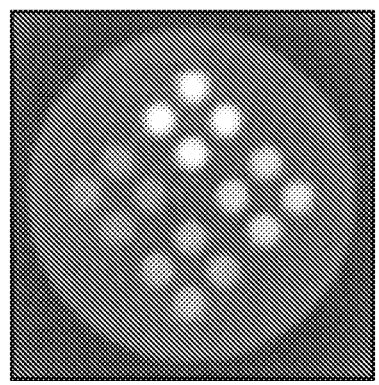
Figure 17C:
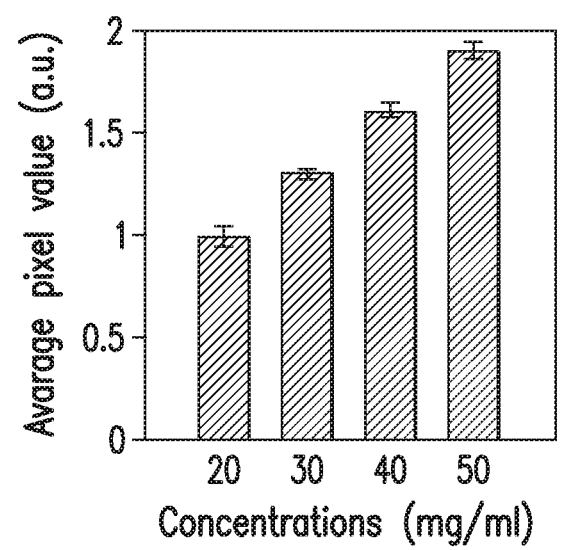

FIGS. 17A-17C show simulated detection and reconstruction results of spectral CT images of the phantom in FIG. 16A. A sinogram of the phantom is showed in FIG. 17A, which was obtained by acquiring 360 X-ray projections around the phantom at a step of 1 degree by the CZT imager, where the ytterbium K-edge energy bin (62 to 76 keV) is set to the projection data. From the detected sinogram, a 3D image of the phantom using the FDK reconstruction algorithm can be reconstructed. FIG. 17B shows a reconstructed tomography at the central section of the phantom with a thickness of 0.5 mm. The pixel values in the image represent the relative attenuation coefficients in the phantom, so the image reveals the attenuation distribution within the phantom. In the image, the four groups of inserts filled with different concentrations of ytterbium can be easily differentiated by the different pixel values within these inserts. To further discriminate these concentrations quantitatively, the average value of the pixels belonging to each insert was calculated, and the calculated average pixel value and the standard error of each group of inserts were showed in FIG. 17C, where the four concentrations of ytterbium were differentiated very well with small deviations.

Figure 18A:
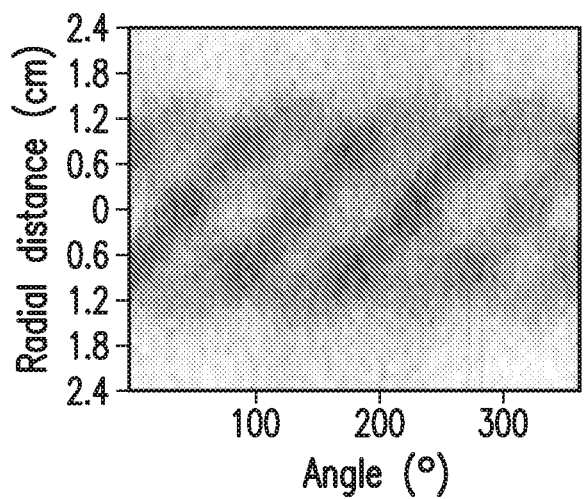
FIGS. 18A-18H show the simulated SPECT detection and reconstruction results of the dual isotope of $^{99m}$Tc and $^{123}$I inserts with different radiation activities shown in the phantom of FIG. 16B.
Figure 18B:
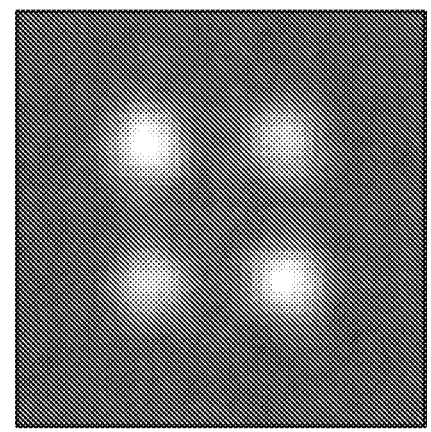
Figure 18C:
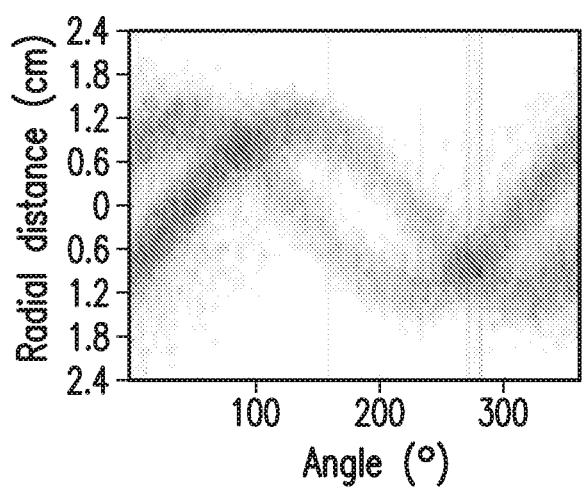

FIGS. 18A-18C show simulated detection and reconstruction results of SPECT images of the phantom in FIG. 16B, wherein the phantom contained two kinds of isotopes ($^{99m}$Tc and $^{123}$I) that can usually be used in clinic in SPECT imaging. FIG. 18A is the detected sinogram of the phantom acquired by the CZT imager around the phantom in full 360, wherein the energy bin was set to include the two photopeaks of the isotope of $^{99m}$Tc and $^{123}$I. The reconstructed tomography from the sinogram is showed in FIG. 18B, where the inserts filled with $^{99m}$Tc and $^{123}$I were displayed clearly in the image. When the energy bin was set to only include the photopeak of the isotope of $^{99m}$Tc, from the sinogram in FIG. 18C, only the projections from the two inserts was visible. The corresponding reconstruction image in FIG. 18D contained only two inserts instead of four inserts in FIG. 18B, and the images of two inserts agreed well with two $^{99m}$Tc inserts in the phantom in FIG. 16B. In the same way, when the energy bin was set to only include the photopeak of the isotope of $^{123}$I, from the sinogram in FIG. 18E and the corresponding reconstruction image in FIG. 18F, only the $^{123}$I inserts can be imaged, and the images of the two $^{123}$I inserts agreed well with the phantom in FIG. 16B.

All the above-mentioned SPECT images were reconstructed by the filtered back-projection (FBP) algorithm, and all the reconstructed tomographic images of the central cross section of the phantom had thickness of 3 mm. The pixel values in the images represent relative radioactive activities within the cross section of the phantom, so the images reveal radioactive activity distribution of the phantom.

Figure 18D:
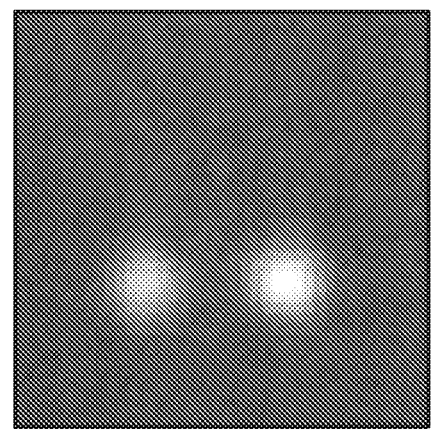
Figure 18E:
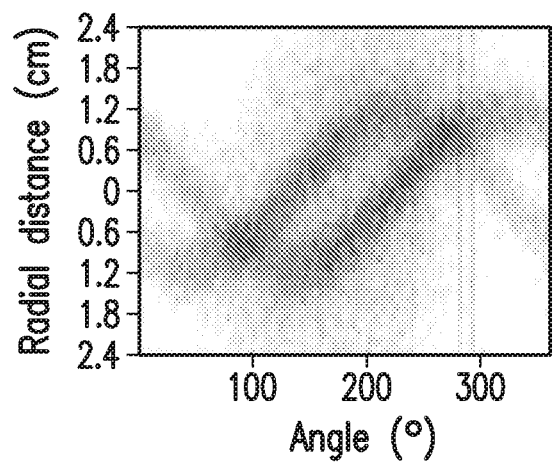
Figure 18F:
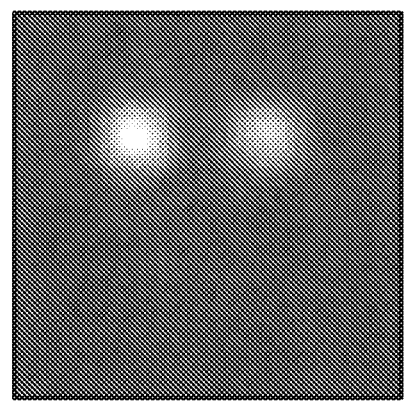
Figure 18G:
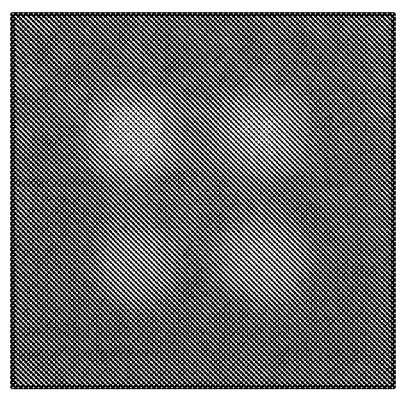
Figure 18H:
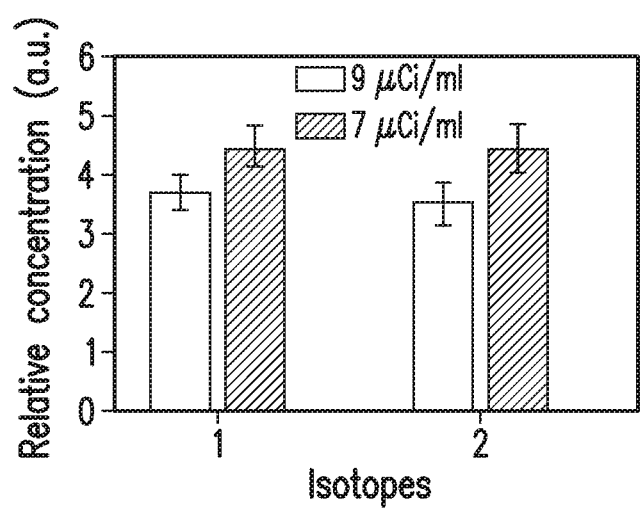

FIG. 18G shows the overlaid image from the images in FIG. 18D and FIG. 18F, where the inserts of the isotope of $^{99m}$Tc and $^{123}$I were reconstructed separately. In the overlaid image, the $^{99m}$Tc inserts and $^{123}$I inserts were displayed in red and green, respectively. To demonstrate the different radiation activity distribution of the isotopes in the phantom, the average values of the pixels that belong to the insert regions were calculated as the relative concentrations of the aqueous solution containing isotopes. FIG. 18H shows the calculated relative concentration of $^{99m}$Tc and $^{123}$I aqueous solution inserts in the phantom, the bars of group "1" and group "2" show two different concentrations of the $^{123}$I and $^{99m}$Tc, respectively.

Figure 19A:
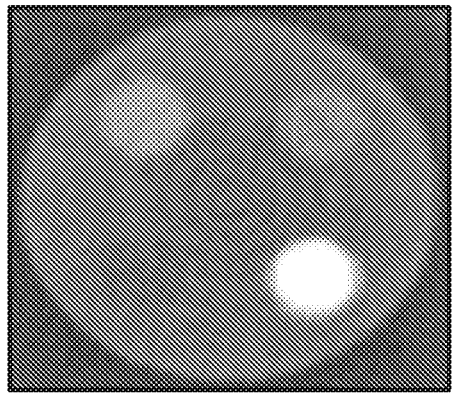
FIGS. 19A-19H demonstrate conventional-CT/spectral-CT/SPECT imaging of the system using the phantom in FIG. 16C.
Figure 19B:
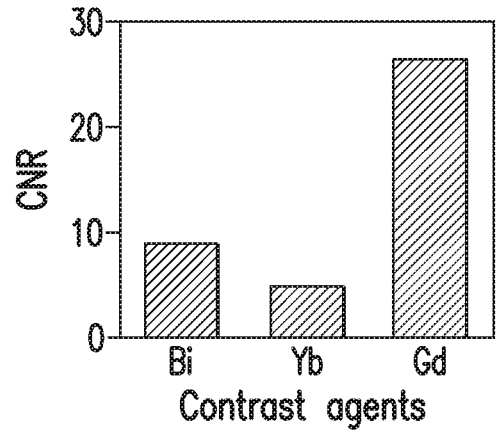
Figure 19C:
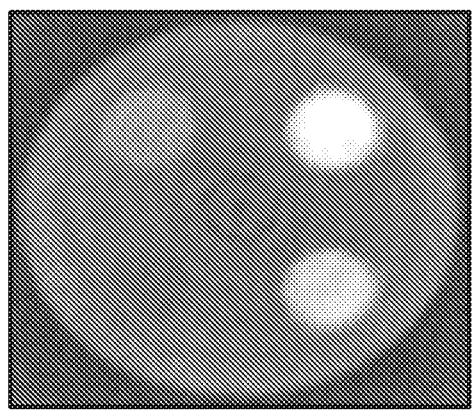
Figure 19D:
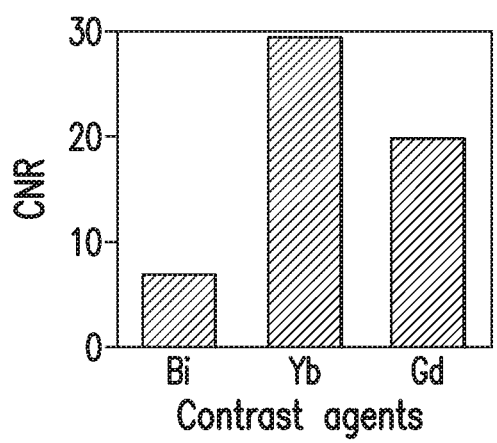
Figure 19E:
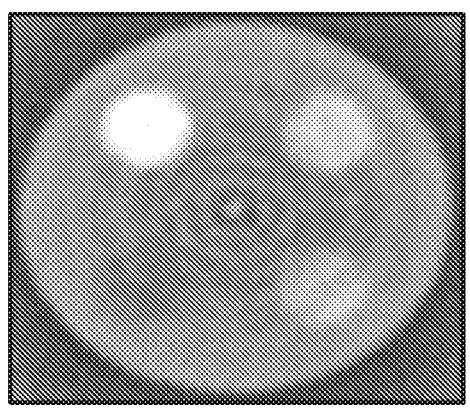
Figure 19F:
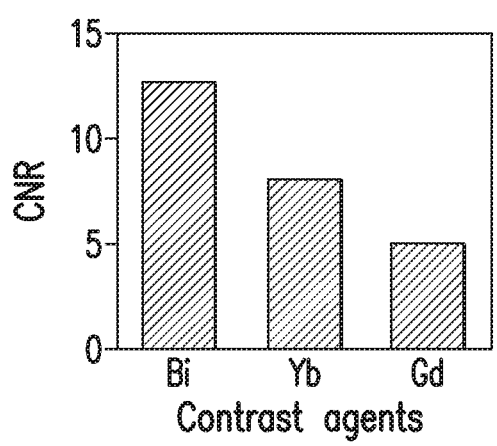

FIGS. 19A-19L show the simulated reconstruction images of the phantom in FIG. 16C. To image a high atomic number element in spectral CT, an energy bin related to the Kedge energy of the element should be selected. In this simulation, the energy bins for the elements of gadolinium, ytterbium and bismuth were selected to be 51 to 62 keV, 62 to 76 keV and 91 to 105 keV, respectively. FIG. 19A shows the reconstruction tomographic image from the K-edge energy bin of gadolinium, and the corresponding contrast-to-noise ratio (CNR) of the contrast agent inserts containing the elements is showed in FIG. 19B, wherein the CNR of the gadolinium insert was much higher than the other two inserts. FIGS. 19C and 19D show the reconstruction tomographic image from the K-edge energy bin of ytterbium and the corresponding CNR of the contrast agent inserts, wherein the CNR of the ytterbium insert was the highest among these contrast agent inserts. In the same way, the bismuth insert shows the highest CNR (FIG. 19F) in the tomographic image in FIG. 19E, which was reconstructed from the bismuth K-edge energy bin.

Figure 19G:
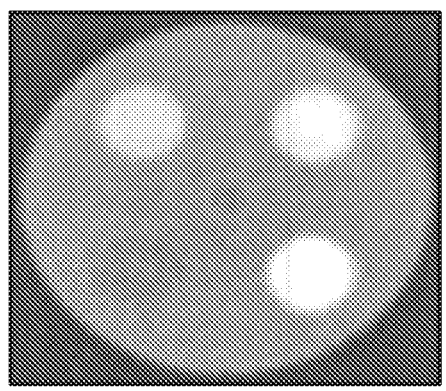
Figure 19H:
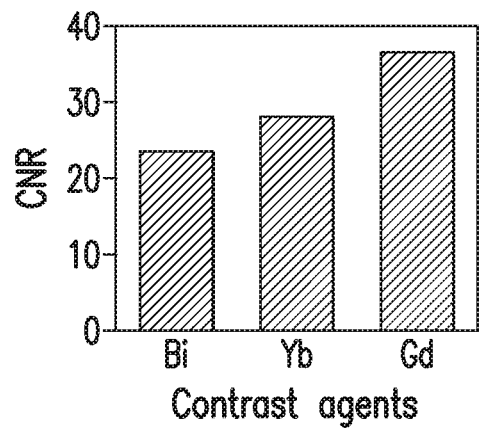

However, when the energy bin can be set to be the whole spectral range (30-130 keV) of the detected photons, the reconstructed tomographic image in FIG. 19G shows no apparent visible difference between the three contrast agents inserts. This can be further demonstrated in the calculated CNRs of the three inserts in FIG. 19H, wherein there was no specifically high CNR related to the K-edge attenuation of these elements, and it just shows the average attenuation of the X-ray photons of these different elements. From FIG. 13, it can be inferred that the average attenuation in the spectral range of 30 to 130 keV of gadolinium was higher than that of ytterbium, which was higher than that of bismuth, so the CNR of the gadolinium insert was the highest while the CNR of the bismuth was the lowest, which can be showed in FIG. 19H.

Figure 19I:
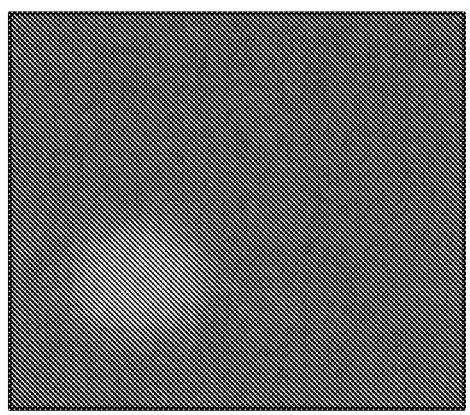
FIGS. 19I-19J show the original and interpolated SPECT images of the $^{99m}$Tc insert in the phantom, respectively.
Figure 19J:
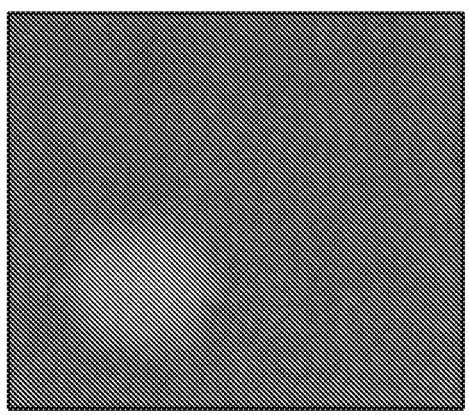
Figure 19K:
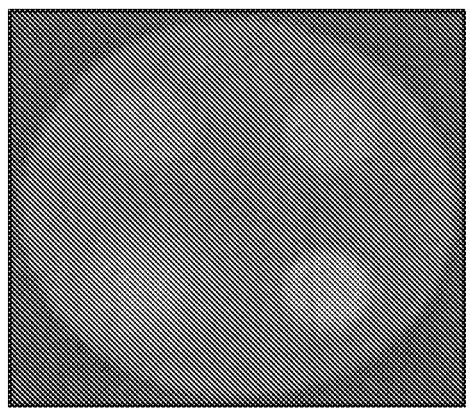
FIGS. 19K-19L show the conventional-CT/SPECT and spectral-CT/SPECT image of the phantom, respectively, wherein the different contrast elements and radiation source can be rendered with different colors in the spectral-CT/SPECT image.
Figure 19L:
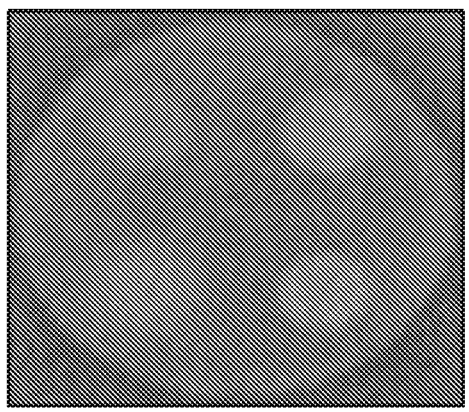

FIGS. 19I and 19J show the reconstructed radiation activity distribution of $^{99m}Tc$ within the phantom in FIG. 16C before and after interpolation, wherein the image of the $^{99m}Tc$ insert agreed well with the phantom. FIGS. 19L and 19L show the overlaid conventional-CT/SPECT image and spectral-CT/SPECT image of the phantom, respectively. In the conventional-CT/SPECT image, the three kinds of contrast agents can hardly be discriminated, while, in the spectral-CT/SPECT image, these three kinds of contrast agents can be clearly differentiated, and can be displayed with different colors.

A pixel value in a spectral CT image represents the average X-ray photon attenuation in a certain energy bin. If different contrast elements with the same concentration can be injected into the subject, one element can be distinguished from another based on its highest average attenuation coefficient in its K-edge energy bin. For example, the insert filled with gadolinium shows the highest photon attenuation in the image of FIG. 19A, which was reconstructed in the gadolinium K-edge energy bin, and the insert filled with ytterbium shows the highest photon attenuation in the image of FIG. 19C, which was reconstructed in the ytterbium K-edge energy bin. In the same way, the insert filled with bismuth shows the highest photon attenuation in the image of FIG. 19E, which was reconstructed in the bismuth K-edge energy bin. Therefore, one element can be differentiated from the other elements due to its highest photon attenuation in its K-edge energy bin.

A pixel value in the SPECT image addresses the relative radiation activity of the isotope labeled radiation pharmaceutical within the subject. The image in FIG. 19I shows the reconstructed radiation activity within the insert filled with $^{99m}Tc$ in the PMMA phantom. Due to the lower space resolution in SPECT imaging compared to spectral CT imaging, a two-dimensional interpolation was conducted to the original SPECT image so that the two modalities of images can be displayed smoothly in one image. The interpolated SPECT image can be shown in FIG. 19J. Comparing the spectral-CT/SPECT image in FIG. 19L to the conventional-CT/SPECT image in FIG. 19K of the phantom, the spectral-CT/SPECT imaging has the apparent advantage of discriminating multiple contrast elements that were injected within the subjects.

It should be noted that, although the K-edge imaging method was used to reconstruct spectral CT images in the simulation, other imaging methods such as projection-based energy weighting imaging and image-based energy weighting imaging and other material decomposing methods can be also included in the present inventive system 200.

Figure 3:
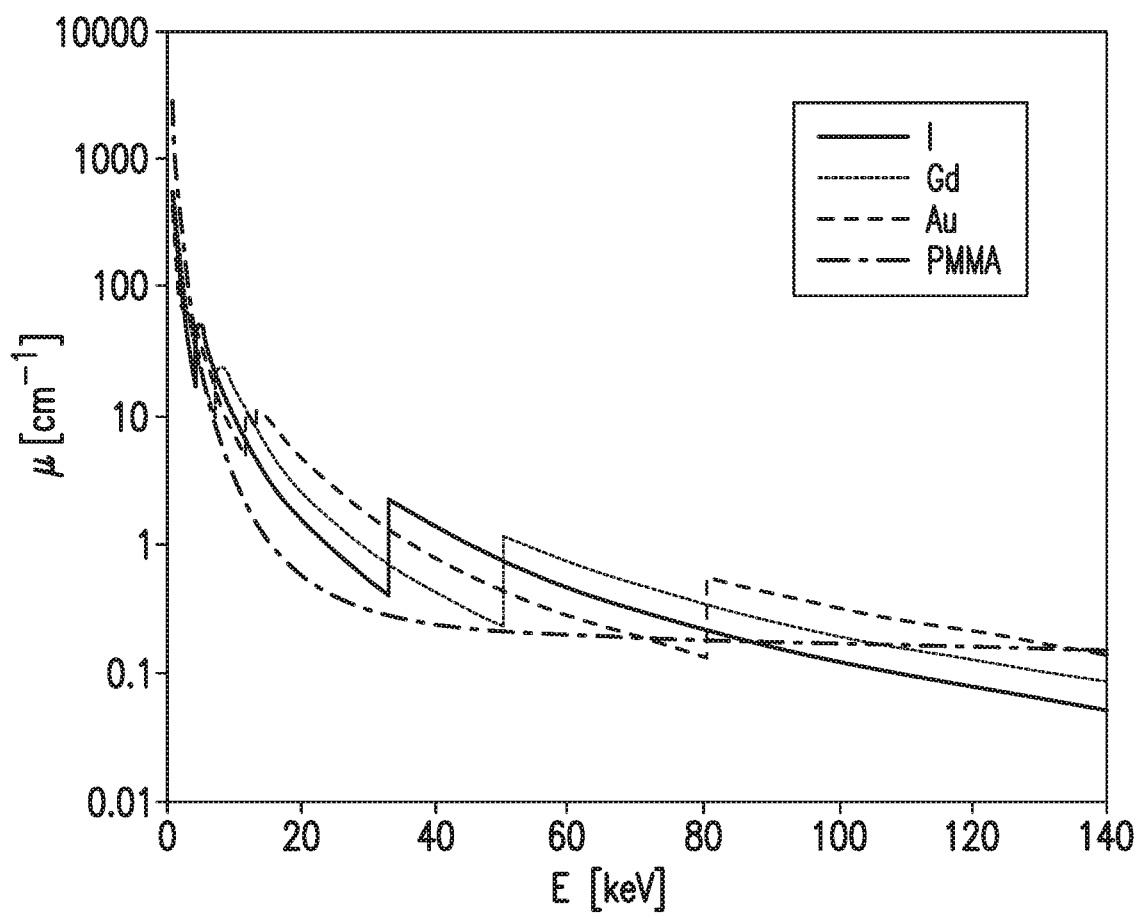
FIG. 3 is a graph that depicts K-edge imaging of multiple example contrast elements in spectral CT imaging.

Experimental Analysis to Determine Diagnostic and Treatment Parameters for a Single Radiation Source System FIG. 3 is a graph that depicts K-edge imaging of multiple example contrast elements in spectral CT imaging. The graph depicts contrast elements that can be used as part of the system 100. For example, the system 100 can use in x-ray spectral-CT imaging with the contrast agents that can be administered to the subject 124, such as contrast agents composed of one or more high atomic number elements such as iodine, gadolinium or gold. The k-edge discontinuities in the linear attenuation coefficients of these elements can be characteristic and unique, and they can be used to discriminate these chemical elements based on their different k-edge absorption energies. For instances, as shown in FIG. 3, the graph compares the example linear attenuation coefficients of iodine (60 mg cm$^{-3}$), gadolinium (60 mg cm$^{-3}$), gold (60 mg cm$^{-3}$) and PMMA (1.195 g cm$^{-3}$), with the example K-edge absorption energies of iodine, gadolinium and gold being 33.2, 50.2, 80.7 keV, respectively.

When polychromatic x-rays traverse the subject 124 injected with contrast agents, the output x-ray spectrum contains discontinue energy-dependent attenuation information of the elements within the contrast agents administered to the subject 124. Choosing appropriate multiple energy windows or bins corresponding to the specific elements, using k-edge imaging method, the components in the contrast agent within the subject can be decomposed and the distribution of these components can be imaged separately by image reconstruction methods (e.g., FDK (Feldkamp, Davis and Kress) reconstruction algorithm) from the detected spectral data sets.

The imager 114 used in the system 100 can be configured to realize k-edge imaging. For example, the imager 114 can be a photon counting imagers using semiconductor materials such as CZT and/or cadmium telluride (CdTe), which can function in pulse mode. Such imagers can have high energy resolution and can provide sufficient spectral information that reveals the distinct k-edge discontinuities linear attenuation of x-rays of the contrast elements within the subject, which can be used to perform spectral CT image with contrast agents. Additionally, such imagers (e.g., CZT imagers) can work at room temperature without the need of special cooling system, which can minimize the cost and complexity of the system 100.

The size of pixels in imager 114 (e.g., CZT imager) can, at least in part, determine the intrinsic resolution of an imaging system. For example, the system 100 can be used for small animal studies, so the imager 114 can be selected to have a pixel size of less than 0.5 mm, which can allow it to be used for both the spectral CT image and the SPECT imaging with a collimator. Each pixel can detect the energy of photons that hit it, which can allow the imager 114 to provide an energy distribution of all the photons that hit the imager 114. To avoid spectral distortion, which can be caused by pulse pile-up effect that can occur with a high photon count rate, the x-ray photon flux can be controlled so that the photon count rate of the imager 114 can be below a threshold value, such as being below $5 \times 10^5$ cps mm$^{-2}$.

Figure 4:
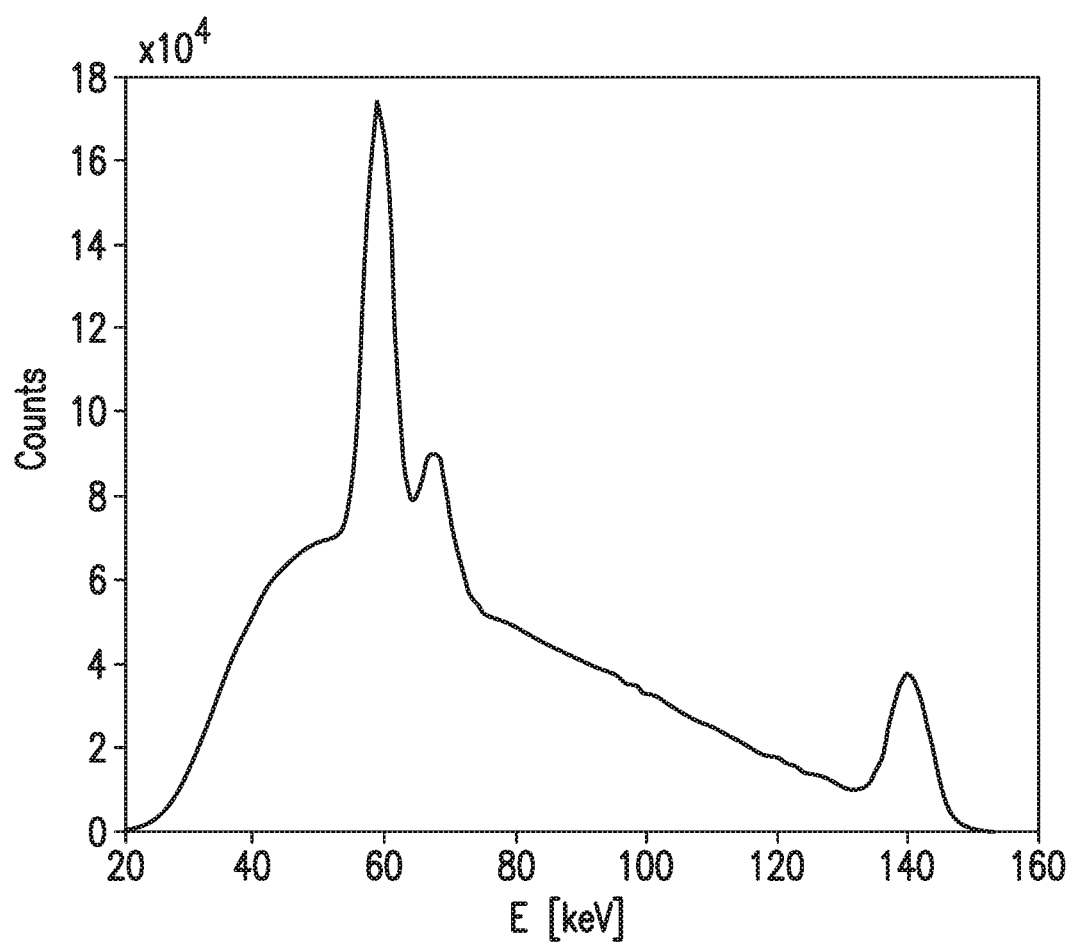
FIG. 4 depicts a graph showing an example energy spectrum of photons detected by a CZT imager.

FIG. 4 depicts a graph showing an example energy spectrum of photons detected by a CZT imager, such as the imager 114. In particular, the graph depicts simulated detection energy spectrum of 140 kVp diagnostic x-ray photons and 140 keV gamma photons from $^{99m}Tc$ by an imager (e.g., CZT imager). Such a simulation can be performed, for example, using simulation software, such as GATE Monte Carlo software. As shown in FIG. 4, the whole spectrum of all the pixels displays that the gamma rays emitted from $^{99m}Tc$ can be readily separated from the x-ray signals based on the energy differences in the spectrum.

Figure 5:
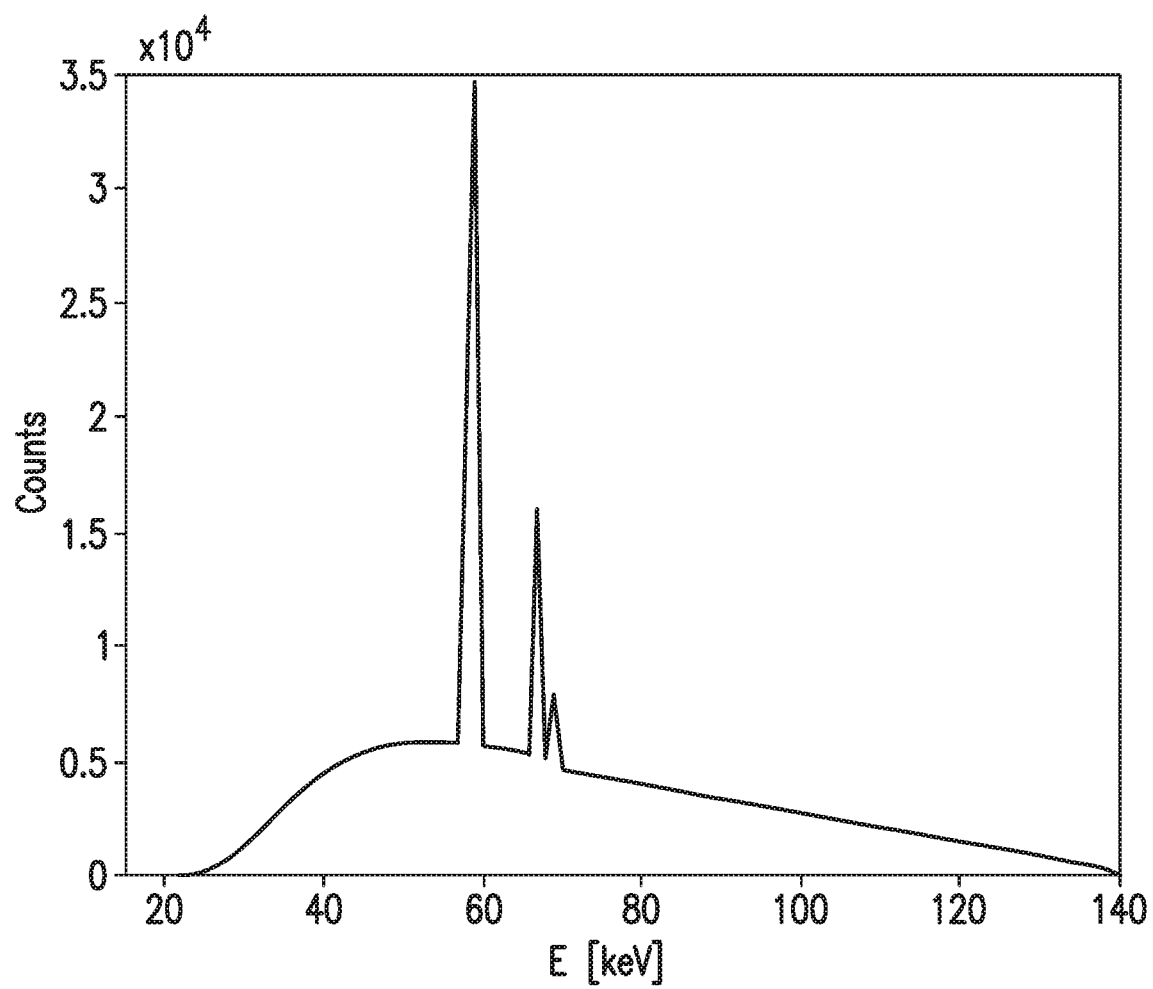
FIG. 5 depicts a graph showing a simulated example x-ray spectral distribution.

FIG. 5 depicts a graph showing a simulated example x-ray spectral distribution. For example, the graph depicts an example spectral distribution of the 140 kVp x-ray beam used for the simulation depicted in FIG. 4. The x-ray photons were simulated as being generated at 140 kVp tube voltage with 3 mm Al filtration in the beam. A variety of techniques can be used for the simulation, such as using the SpekCalc program.

FIGS. 6A-C show various phantoms that used in simulations to investigate the performance of spectral-CT/SPECT imaging. Such phantoms can be used to simulate and investigate the performance of the example system 100, and can include various numbers, sizes, and/or compositions. For example, to investigate the performance of spectral-CT image subsystems in discriminating between different concentrations of the same contrast element at the same k-edge energy bin, a cylindrical polymethylmethacrylate (PMMA) phantom with five inserts filled with different concentrations of iodine contained aqueous solution were simulated for imaging, as depicted in FIG. 6A. Example simulated concentrations of iodine inserts that were used include 10, 20, 30, 40, 50 mg ml$^{-1}$ in order, respectively. The selected k-edge energy bin used in the simulations ranged from 34 to 48 keV, which was based on previously determined energy bins of k-edge image of iodine element according to earlier studies.

For example, simulations can use five iodine inserts with different concentrations in a PMMA cylinder, a three $^{99m}$Tc inserts with different radiation activities in a PMMA cylinder, and a five multiple contrast (including iodine, gadolinium, gold, mixture of the three above elements, and a radiation source from $^{99m}$Tc) inserts in a PMMA cylinder.

To investigate the performance of SPECT subsystem to identify different activity distributions of a radioactive tracer within the subject, a cylindrical PMMA phantom with three inserts filled with aqueous solutions of $^{99m}$Tc at concentration of 30, 40, 50 µCi ml$^{-1}$, respectively, was simulated for imaging, as depicted in FIG. 6B. To reduce image blurring caused by the photons from scattering, an energy threshold was set for detecting the photons.

Referring to FIG. 6C, to demonstrate the performance of combined conventional-CT/spectral-CT/SPECT imaging of the example system 100, a cylindrical PMMA phantom with five inserts was simulated for imaging. The five inserts were filled with aqueous solution containing element of iodine (30 mg ml$^{-1}$), gadolinium (30 mg ml$^{-1}$), gold (30 mg ml$^{-1}$), mixture of the three elements (at equivalent concentration of 30 mg ml$^{-1}$) and radioactive $^{99m}$Tc (50 µCi ml$^{-1}$), respectively.

In one example simulation of the system 100 for imaging, an x-ray focus to central axis of rotation distance of 400 mm and an x-ray focus to imager distance of 450 mm were designed, and a pixelated CZT imager with a thickness of 4 mm was modeled. The imager had an 80×80 array of pixels, a pixel pitch of 0.5×0.5 mm$^2$ and a size of 40×40 mm$^2$. A high-resolution lead collimator with parallel quadrate holes was designed to match the pixel size of the CZT imager for SPECT imaging. It had a length of 20 mm, a hole width of 0.45 mm and a septa width of 0.1 mm. As mentioned above, the cylindrical PMMA phantoms with a diameter of 18 mm filled within different inserts were used to demonstrate the imaging performance of the system 100.

Figure 7A:
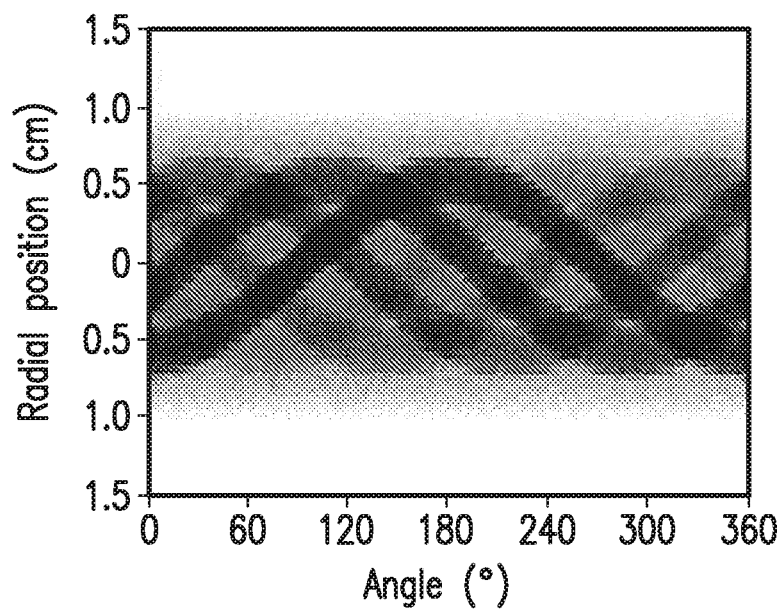
FIGS. 7A-7C depict example simulated detection and reconstruction images of the phantoms from FIG. 6A using a spectral CT subsystem.
Figure 7B:
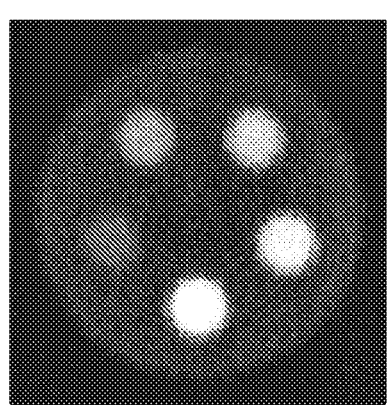
Figure 7C:
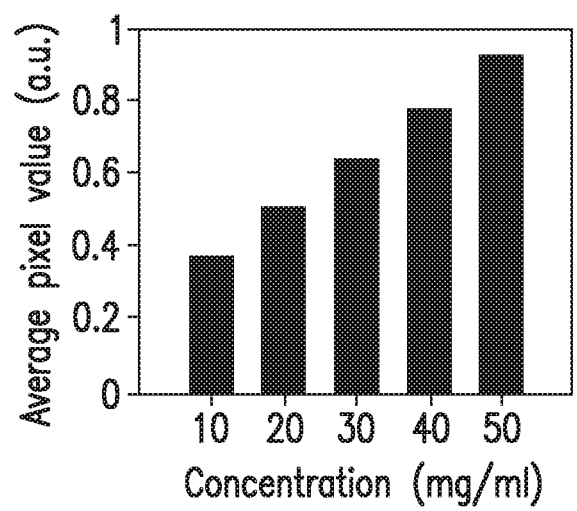

FIGS. 7A-C show example simulated detection and reconstruction images of the phantoms from FIG. 6A using a spectral CT subsystem. FIG. 7A depicts a sinogram of phantoms that can be developed from acquiring 360° x-ray projections around the phantoms at a step of 1° by the imager 114 (e.g., CZT imager). From the projection data of the sinograms, a 3D image of the phantom using, for example, an FDK reconstruction algorithm can be generated. FIG. 7B shows an example reconstructed tomography at the central section of an example phantom with a thickness of 0.25 mm. The pixel values in the image represent the relative attenuation coefficients in the phantom, so the image reveals the attenuation distribution within the phantom. In the example image depicted in FIG. 7B, the five inserts filled with different concentration of iodine can be identified visually by the different pixel values within these inserts. FIG. 7C depicts a graph of the average value of the pixels belonging to each insert was calculated. Such average values can be used to further quantitatively discriminate between the five example concentrations of iodine.

Figure 8A:
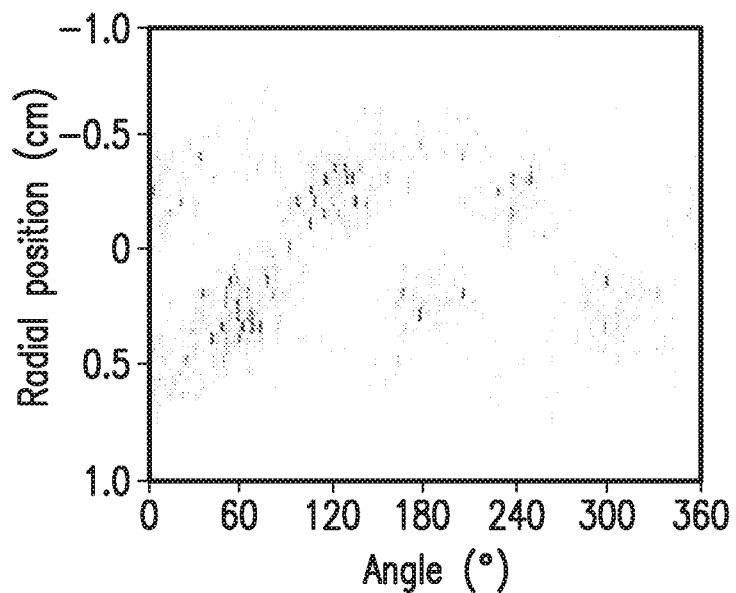
FIGS. 8A-8C depict example simulated detection and reconstruction images of the phantoms embedded with radioisotope of FIG. B using a SPECT subsystem.
Figure 8B:
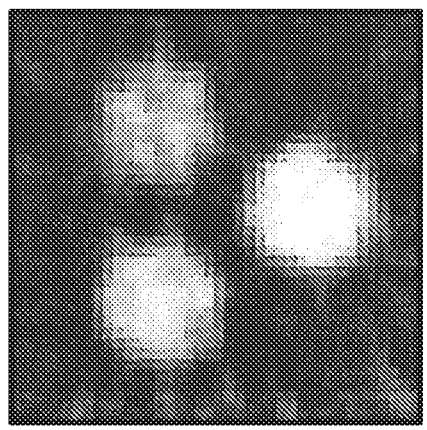
Figure 8C:
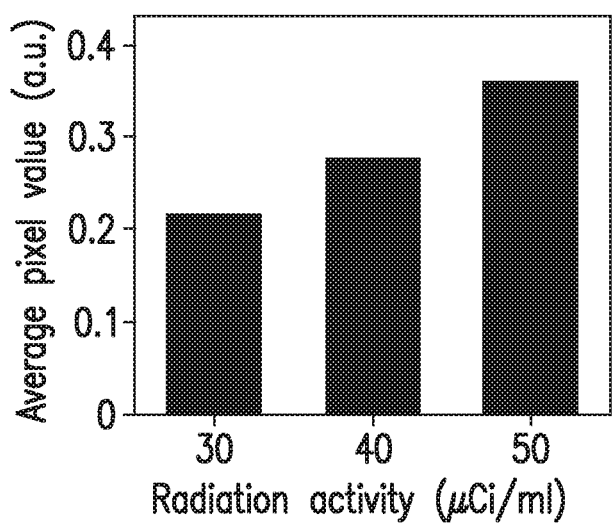

FIGS. 8A-C depict example simulated detection and reconstruction images of the phantoms embedded with radioisotope of FIG. 6B using a SPECT subsystem. FIG. 8A depicts an example detected sinogram of the phantom acquired by rotating the imager 114 (e.g., CZT imager) around the phantom in full 360°. FIG. 8B depicts an example reconstruction image that can be generated from the sinogram by using, for example, a filtered backprojection algorithm. The example reconstruction image can be a tomography image of a central cross section of the phantom with an example thickness of 1.5 mm. The pixel values in the image represent relative radioactive activity within the cross section of the phantom, so the image reveals the radioactive activity distribution in the phantom. In the image, three regions can be identified with different radioactive activities, which can be corresponding to the three inserts with different radiation activities of $^{99m}$Tc within the phantom. FIG. 8C shows a graph depicting the average values of the pixels that belong to the three insert regions. Such calculations can be used to quantitatively detect the different radiation concentration of the $^{99m}$Tc within the inserts.

Figure 9A:
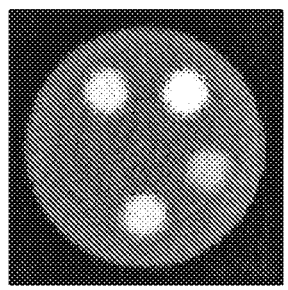
FIGS. 9A-9H depict example simulated reconstruction images of the phantom of FIG. 6C through combinations of conventional-CT/spectral-CT/SPECT imaging.
Figure 9B:
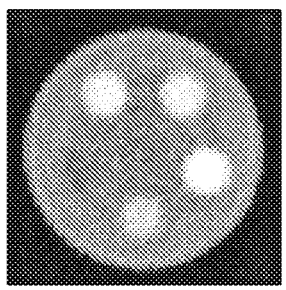
Figure 9C:
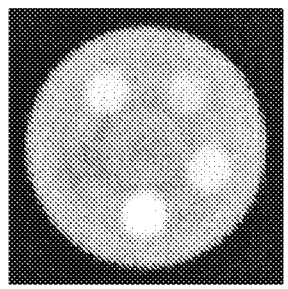
Figure 9D:
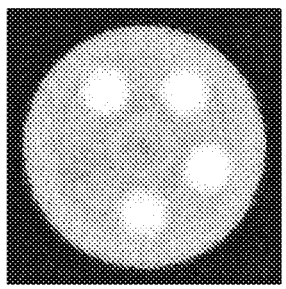
Figure 9E:
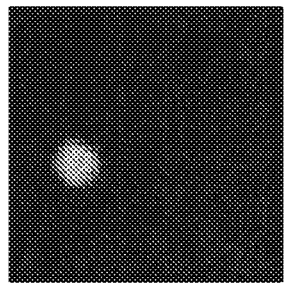
Figure 9F:
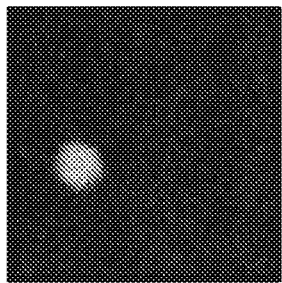
Figure 9G:
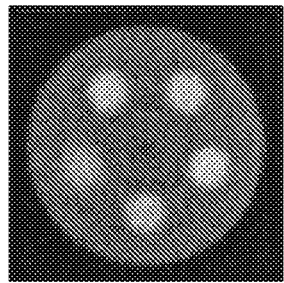
Figure 9H:
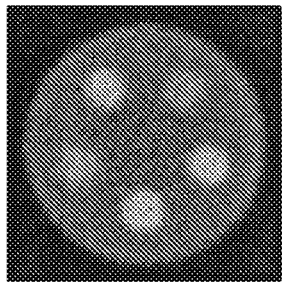

FIGS. 9A-H depict example simulated reconstruction images of the phantom of FIG. 6C through combinations of conventional-CT/spectral-CT/SPECT imaging. The example combined imaging can be generated by, for example, the system 100. To image a high atomic number element, an energy bin related to the K-edge energy of the element was selected. In this simulation, the energy bins for the elements iodine, gadolinium, and gold were selected to be 34 to 48 keV, 50 to 65 keV and 80 to 95 keV, respectively. FIGS. 9A-C show the reconstructed tomography images from the K-edge energy bin of iodine, gadolinium, and gold, respectively. FIG. 9D shows the reconstructed conventional CT image with the whole spectral range x-ray photons. FIGS. 9E-F show the reconstructed radiation activity of $^{99m}$Tc of the insert within the phantom before and after interpolation. FIG. 9G shows the overlaid tomography image of the radiation tracer in the phantom and the conventional CT image of the multiple contrast elements in the phantom. FIG. 9H shows the overlaid spectral CT image of the multiple contrast elements and the radiation tracer in the phantom, where the different elements and the radiation tracer were rendered with different colors for identification.

Pixel values in spectral-CT images can represent the average x-ray photon relative attenuation coefficients within certain energy bins. If different contrast elements with the same concentration can be injected into the subject 124, one element can be distinguished from another based on its highest average attenuation coefficient in its k-edge energy bin. For example, an insert filled with iodine element may only show the highest photon attenuation in the image of FIG. 9A using the iodine k-edge energy bin, and the insert filled with gadolinium element may only shows the highest photon attenuation in the image of FIG. 9B using the gadolinium k-edge energy bin. Similarly, the insert filled with gold element may only shows the highest photon attenuation in the image of FIG. 9C using the gold k-edge energy bin. Additionally, an insert filled with the three elements with the same equivalent concentration to the abovementioned three inserts may show the approximately average photon attenuation of the three elements in the images of FIGS. 9A-9C using k-edge energy bins of each element.

Pixel values in SPECT images can represent the relative radiation activity of a radiation tracer and/or pharmaceutical within the subject 124. For example, the image in FIG. 9E shows the reconstructed radiation activity within the insert filled with $^{99m}$Tc in a PMMA phantom. Due to the lower spatial resolution in SPECT imaging compared to spectral CT imaging, a two-dimensional interpolation can be performed on the original SPECT image so that the two modalities of images can be showed smoothly in co-registered image. An example interpolated SPECT image can be showed in FIG. 9F, and the final overlaid image corresponding to all the inserts in the phantom can be showed in FIG. 9H, where the different inserts can be distinguished with different visual features (e.g., colors). Inserts containing contrast elements, which may be difficult to discern using conventional CT imaging, can be displayed (e.g., in grey) and overlaid conventional CT and SPECT images, as depicted in FIG. 9G.

The above description describes only the exemplary embodiments of the disclosure, modification and changes made by others can be within the scope of the following claims.

What is claimed is:

1. A radiotherapy system comprising:
   a first radiation source that is configured to emit a first radiation beam for imaging a subject;
   a first imager that is positioned opposite the first radiation source to detect the first radiation beam after the first radiation beam has traversed the subject, wherein the first imager is configured to detect plurality of different types of images of the subject;
   a second radiation source that is configured to emit a second radiation beam to provide radiotherapy to the subject;
   a second imager that is positioned opposite the second radiation source to detect the second radiation beam after the second radiation beam has traversed the subject, wherein the second imager is configured to detect at least one type of image of the subject; and
   a computer system that is programmed to:
      combine the types of images of the subject into a comprehensive image of the subject;
      identify one or more target areas within the subject for treatment based, at least in part, on the comprehensive image of the subject;
      determine one or more treatment characteristics for the one or more target areas based, at least in part, on the comprehensive image of the subject and the one or more target areas; and
      control delivery of the radiotherapy treatment to the one or more target areas within the subject according to the one or more treatment characteristics,
   wherein the first imager is configured to produce a conventional-computed tomography (CT) image type, a spectral-CT image type, and a single photon emissions computed tomography (SPECT) image type.

2. The radiotherapy system of claim 1, further comprising:
   a first collimator that is positioned between the first imager and the subject, and that is configured to direct one or more types of radiation from the subject to the first imager.

3. The radiotherapy system of claim 2, wherein:
   the one or more types of radiation comprise gamma rays, and
   the first imager is configured to detect the gamma rays.

4. The radiotherapy system of claim 2, wherein the first collimator comprises a high resolution collimator with one or more surfaces defining holes that are specifically sized or shaped.

5. The radiotherapy system of claim 4, wherein the holes are sized to correspond to the size of pixels in the imager.

6. The radiotherapy system of claim 4, wherein the high resolution collimator comprises a parallel square hole collimator.

7. The radiotherapy system of claim 1, wherein the first and second radiation sources comprise respective x-ray radiation sources.

8. The radiotherapy system of claim 1, wherein the first imager comprises a photon counting imager that is configured to receive photons from a radiation beam that has traversed the subject.

9. The radiotherapy system of claim 8, wherein the photon counting imager comprises a cadmium zinc telluride (CZT) imager.

10. The radiotherapy system of claim 1, wherein the first radiation source comprises an x-ray radiation source and the first radiation beam comprises an x-ray beam.

11. The radiotherapy system of claim 10, wherein the x-ray radiation source comprises an x-ray tube.

12. The radiotherapy system of claim 10, wherein the first radiation source is configured to emit the first radiation beam at a plurality of low energy levels for imaging the subject and the second radiation source is configured to emit the second radiation at a high energy level that is higher than the low energy levels of the first radiation beam to provide the radiotherapy to the subject.

13. The radiotherapy system of claim 12, wherein the plurality of low energy levels range from about 70 kVp to about 150 kVp.

14. The radiotherapy system of claim 12, wherein the high energy level ranges from about 6 MV to about 10 MV.

15. The radiotherapy system of claim 1, wherein the first imager detects the plurality of different types of images of the subject in advance of the radiotherapy treatment being delivered to the subject.

16. The radiotherapy system of claim 1, wherein:
   the computer system is programmed to repeatedly perform the combining, the identifying, the determining, and the controlling while the radiotherapy treatment is being delivered.

17. The radiotherapy system of claim 1, further comprising:
   a gantry that is rotatable about a central axis,
   wherein the first radiation source, the first imager, the second radiation source, and the second imager are mounted to the gantry, and
   wherein the computer system is further programmed to control rotation of the gantry according to the one or more treatment characteristics.

18. The radiotherapy system of claim 1, wherein the first imager is a cadmium zinc telluride (CZT) imager.

19. The radiotherapy system of claim 18, wherein the CZT imager in configured to work in photon-pulse-counting mode.

20. The radiotherapy system of claim 1, further comprising:
   a moveable support structure configured to support the subject in a desired orientation relative to the first and second radiation sources,
   wherein the computer system is further programmed to control movement of the moveable support structure.

21. A radiotherapy system for the treatment of a subject, the radiotherapy system comprising:
   at least one radiation source that is configured to emit a radiation beam for imaging a subject and/or providing radiotherapy treatment to the subject;

at least one imager that is positioned opposite a corresponding radiation source to detect the radiation beam emitted by the corresponding radiation source after the radiation beam has traversed the subject, wherein the at least one imager is configured to detect a plurality of different types of images of the subject;

a computer system that is programmed to:
combine the plurality of different types of images of the subject into a comprehensive image of the subject;
identify one or more target areas within the subject for treatment based, at least in part, on the comprehensive image of the subject;
determine one or more treatment characteristics for the one or more target areas based, at least in part, on the comprehensive image of the subject and the one or more target areas; and
control delivery of the radiotherapy treatment by the at least one radiation source to the one or more target areas within the subject according to the one or more treatment characteristics, wherein the at least one imager comprises a first imager that is configured to produce a conventional-computed tomography (CT) image type, a spectral-CT image type, and a single photon emissions computed tomography (SPECT) image type.

22. A method comprising:
using a radiotherapy system to image a subject and/or to deliver radiation treatment to the subject, the radiotherapy system comprising:
a first radiation source that is configured to emit a first radiation beam for imaging a subject;
a first imager that is positioned opposite the first radiation source to detect the first radiation beam after the first radiation beam has traversed the subject, wherein the first imager is configured to detect plurality of different types of images of the subject;
a second radiation source that is configured to emit a second radiation beam to provide radiotherapy to the subject;
a second imager that is positioned opposite the second radiation source to detect the second radiation beam after the second radiation beam has traversed the subject, wherein the second imager is configured to detect at least one type of image of the subject; and
a computer system that is programmed to:
combine the types of images of the subject into a comprehensive image of the subject;
identify one or more target areas within the subject for treatment based, at least in part, on the comprehensive image of the subject;
determine one or more treatment characteristics for the one or more target areas based, at least in part, on the comprehensive image of the subject and the one or more target areas; and
control delivery of the radiotherapy treatment to the one or more target areas within the subject according to the one or more treatment characteristics, wherein the first imager is configured to produce a conventional-computed tomography (CT) image type, a spectral-CT image type, and a single photon emissions computed tomography (SPECT) image type.

23. The method of claim 22, further comprising:
using the first radiation source to emit a first radiation beam for imaging a subject;
using the first imager to detect the first radiation beam after the first radiation beam has traversed the subject, wherein the first imager detects a plurality of different types of images of the subject;
using the second radiation source to emit a second radiation beam to provide radiotherapy to the subject;
using the second imager to detect the second radiation beam after the second radiation beam has traversed the subject, wherein the second imager detects at least one type of image of the subject; and
using the computer system to:
combine the types of images of the subject into a comprehensive image of the subject;
identify one or more target areas within the subject for treatment based, at least in part, on the comprehensive image of the subject;
determine one or more treatment characteristics for the one or more target areas based, at least in part, on the comprehensive image of the subject and the one or more target areas; and
control delivery of the radiotherapy treatment to the one or more target areas within the subject according to the one or more treatment characteristics.

24. A radiotherapy system comprising:
a first radiation source that is configured to emit a first radiation beam for imaging a subject;
a first imager that is positioned opposite the first radiation source to detect the first radiation beam after the first radiation beam has traversed the subject, wherein the first imager is configured to detect plurality of different types of images of the subject;
a second radiation source that is configured to emit a second radiation beam to provide radiotherapy to the subject;
a second imager that is positioned opposite the second radiation source to detect the second radiation beam after the second radiation beam has traversed the subject, wherein the second imager is configured to detect at least one type of image of the subject; and
a computer system that is programmed to:
combine the types of images of the subject into a comprehensive image of the subject;
identify one or more target areas within the subject for treatment based, at least in part, on the comprehensive image of the subject;
determine one or more treatment characteristics for the one or more target areas based, at least in part, on the comprehensive image of the subject and the one or more target areas; and
control delivery of the radiotherapy treatment to the one or more target areas within the subject according to the one or more treatment characteristics, wherein the computer system is programmed to repeatedly perform the combining, the identifying, the determining, and the controlling while the radiotherapy treatment is being delivered.

* * * * *